United States Patent [19]

Urban

[11] Patent Number: 4,935,442
[45] Date of Patent: * Jun. 19, 1990

[54] TETRAHYDROFURAN-CONTAINING MACROCYCLIC POLYETHER CARBOXYLIC ACIDS

[75] Inventor: Frank J Urban, Waterford, Conn.

[73] Assignee: Pfizer Inc., New York, N.Y.

[*] Notice: The portion of the term of this patent subsequent to Oct. 11, 2005 has been disclaimed.

[21] Appl. No.: 393,832

[22] Filed: Aug. 14, 1989

Related U.S. Application Data

[63] Continuation of Ser. No. 919,180, filed as PCT US85/00338 on Feb. 28, 1985, abandoned.

[51] Int. Cl.$^5$ .................. A61K 31/335; C07D 323/00
[52] U.S. Cl. .................................... 514/450; 549/349; 549/351
[58] Field of Search ................. 549/349, 351; 514/450

[56] References Cited

U.S. PATENT DOCUMENTS

| | | | |
|---|---|---|---|
| 3,580,889 | 5/1971 | Barney et al. | 549/349 |
| 3,686,225 | 8/1972 | Pedersen | 549/349 |
| 3,839,557 | 10/1974 | Raun | 424/115 |
| 3,952,015 | 4/1976 | Krespan | 540/466 |
| 3,965,116 | 6/1976 | Cram | 549/349 |
| 4,777,270 | 10/1988 | Urban | 549/349 |

OTHER PUBLICATIONS

J. Amer. Chem. Soc., vol. 97, 1257 (1975).
J. Amer. Chem. Soc., vol. 96, 7159 (1974).
J. Amer. Chem. Soc., vol. 99, 4207 (1977).
J. Amer. Chem. Soc., vol. 98, 4018 (1976).
J. Amer. Chem. Soc., vol. 98, 7414 (1976).
J. Amer. Chem. Soc., vol. 100, 2828 (1978).
J. Amer. Chem. Soc., vol. 96, 7097 (1974).
J. Amer. Chem. Soc., vol. 104, 5185 (1982).
Tetrahedron Letters, No. 25, 2105 (1975).
Endeavour, vol. 30, 142 (1971).
Tetrahedron, vol. 32, 1161 (1976).
Recueil, J. Roy. Neth. Chem. Soc., vol. 95, 258 (1976).

*Primary Examiner*—Glennon H. Hollrah
*Assistant Examiner*—Ba K. Trinh
*Attorney, Agent, or Firm*—Peter C. Richardson; J. Trevor Lumb

[57] ABSTRACT

A series of tetrahydrofuran-containing, macrocyclic polyether compounds. The macrocycles have a 21-membered ring, incorporating six oxygen atoms, and they have a carboxy group (or a salt thereof) directed towards the interior of the ring. Administration of the compounds of the invention to ruminant animals (e.g. cattle and sheep) modifies their digestive fermentation processes such that the volatile fatty acids produced in the rumen contain a higher proportion of propionates rather than acetates, thereby increasing the efficiency of feed utilization in said ruminant animals. Additionally, the compounds of the invention show antibacterial activity in vitro against certain gram-positive microorganisms.

20 Claims, No Drawings

TETRAHYDROFURAN-CONTAINING MACROCYCLIC POLYETHER CARBOXYLIC ACIDS

CROSS-REFERENCE TO RELATED APPLICATIONS

This application is a continuation of application Ser. No. 06/919,180 filed Sept. 8, 1986, now abandoned, which in turn matured from International Application No. PCT/US85/00338, filed Feb. 28, 1985.

TECHNICAL FIELD

The efficiency of feed utilization in domestic animals, especially the ruminants such as cattle and sheep, is of economic importance in the farming industry. For this reason, attempts have been made to increase the efficiency with which ruminants utilize their food.

As an aid to discovering methods of increasing the efficiency of feed utilization in ruminants, studies on the biochemical mechanisms by which ruminants digest and degrade food, particularly carbohydrates, has been widely studied. It is now known that carbohydrates are degraded in the rumen to monosaccharides, which are converted to pyruvates, and thence to acetates and propionates. Additionally acetates recombine in the rumen to some extent to form butyrates. These acetates, propionates and butyrates, collectively known as volatile fatty acids (or VFA's), are all used as energy sources by ruminants. However, the conversion of pyruvates to acetates involves chain-shortening by one carbon atom, and this carbon atom is lost in the form of methane gas. Thus the production of propionates from carbohydrates in the rumen of ruminant animals represents a more energy-efficient degradative pathway than the production of acetates and butyrates.

As a result, treatment of a ruminant so as to cause a shift in VFA ratios in the rumen towards increased rumen propionic acid (RPA) leads to a beneficial effect on ruminant growth for a given amount of food consumption. Thus there is increased efficiency of feed utilization.

BACKGROUND ART

Several, naturally-occurring, polyether antibiotics (e.g. monensin) have been reported to increase feed utilization in ruminants; U.S. Pat. No. 3,839,557. A variety of macrocyclic polyether compounds having a carboxy group directed into the polyether ring have been described in U.S. Pat. No. 3,965,116 and *Journal of the American Chemical Society*, 97, 1257 (1975), but none of these compounds was reported to have feed utilization efficiency increasing properties.

DISCLOSURE OF INVENTION

This invention provides a series of new chemical compounds which increase rumen propionic acid production in ruminant animals when administered orally to ruminants, at a low level, daily. These new chemical compounds are macrocyclic polyether compounds, which have a 21-membered ring, containing six oxygen atoms, and also have a carboxy group directed towards the interior of the polyether ring.

More particularly, this invention provides a novel macrocyclic polyether compound selected from the group consisting of

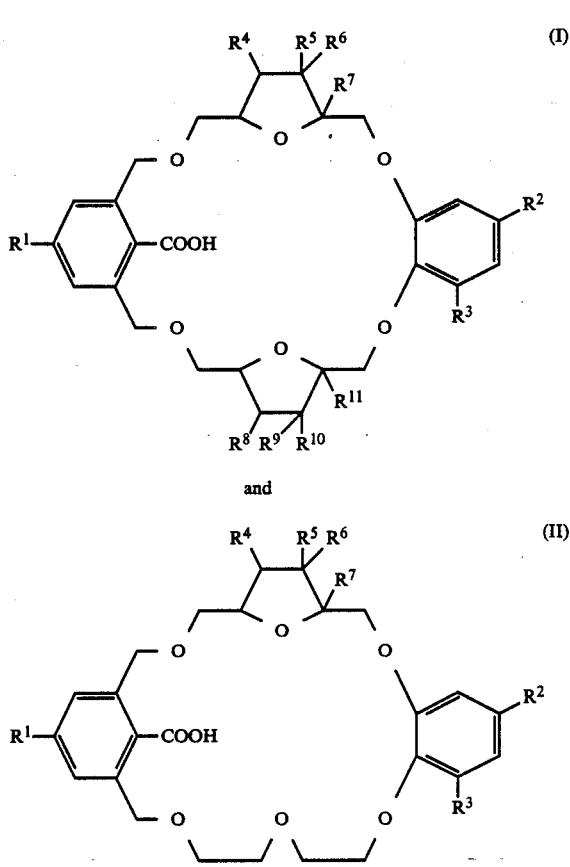

and the pharmaceutically-acceptable base salts thereof, wherein
- $R^1$ is selected from the group consisting of hydrogen and t-butyl;
- $R^2$ is selected from the group consisting of hydrogen, alkyl having 1 to 10 carbons and phenyl;
- $R^3$ is selected from the group consisting of hydrogen, alkyl having 1 to 8 carbons and thiophenoxymethyl;
- and $R^4$, $R^5$, $R^6$, $R^7$, $R^8$, $R^9$, $R^{10}$ and $R^{11}$ are each selected from the group consisting of hydrogen and methyl, provided that not more than two of $R^4$, $R^5$, $R^6$ and $R^7$ are methyl and not more than two of $R^8$, $R^9$, $R^{10}$ and $R^{11}$ are methyl.

Said compounds of the formula I and II are useful for administration to ruminant animals, e.g. cattle and sheep, for the purpose of increasing the efficiency of feed utilization. Additionally, said compounds of formula I and II are active as antibacterial agents in vitro against certain gram-positive microorganisms, e.g. *Staphylococcus aureus*.

A first preferred group of compounds of this invention consists of the compounds of formula I, wherein $R^1$ is t-butyl; $R^2$ is as defined previously; $R^3$ is hydrogen or said alkyl; and $R^4$, $R^5$, $R^6$, $R^7$, $R^8$, $R^9$, $R^{10}$ and $R^{11}$ are each hydrogen.

A second preferred group of compounds of this invention consists of the compounds of formula I, wherein $R^1$ is t-butyl; $R^2$ is as defined previously; $R^3$ is hydrogen or said alkyl; $R^4$, $R^5$, $R^6$, $R^8$, $R^9$, and $R^{10}$ are each hydrogen; and $R^7$ and $R^{11}$ are each methyl.

Especially valuable individual compounds of the invention are:

(a) the compound of formula I, wherein $R^1$ is t-butyl; $R^2$ is t-octyl; and $R^3$, $R^4$, $R^5$, $R^6$, $R^7$, $R^8$, $R^9$, $R^{10}$ and $R^{11}$ are each hydrogen; and (b) the compound of formula I, wherein $R^1$ is t-butyl; $R^2$ is t-octyl; $R^3$, $R^4$, $R^5$, $R^6$, $R^8$, $R^9$ and $R^{10}$ are each hydrogen; and $R^7$ and $R^{11}$ are each methyl.

DETAILED DESCRIPTION

This invention relates to the new chemical compounds of formulae I and II. These are large-ring (21-membered) polyether compounds, and the large ring further incorporates two aromatic fragments, one aromatic fragment being a 1,3-disubstituted benzene ring and the other aromatic fragment being 1,2-disubstituted benzene ring. Moreover, these benzene rings can carry substituents and, in general, substituents which increase the lipophilicity of the parent macrocycle are desirable for imparting feed utilization efficiency increasing properties. For example, these substituents can be straight- or branched-chain alkyl groups, and particular alkyl groups which are commonly used are the tertiary butyl (t-butyl) group and the group of the formula —C(CH$_3$)$_2$—CH$_2$—C(CH$_3$)$_3$. The latter group is named systematically as the 1,1,3,3,-tetramethylbutyl group; however, for convenience in this specification, this group is referred to by its trivial name, t-octyl.

The compounds of formula I and II are usually obtained by hydrolysis of the corresponding ester compound of the formula

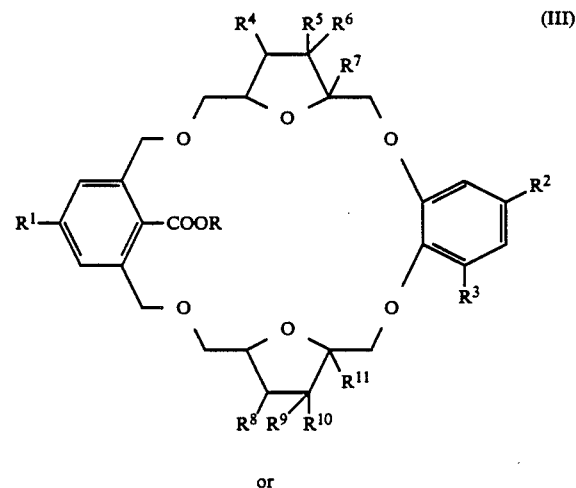

(III)

or

-continued

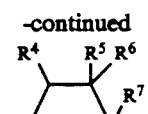

(IV)

wherein $R^1$, $R^2$, $R^3$, $R^4$, $R^5$, $R^6$, $R^7$, $R^8$, $R^9$, $R^{10}$ and $R^{11}$ are as defined previously, and R is a lower-alkyl group (e.g. an alkyl having 1 to 5 carbons), by basic hydrolysis. Favorably, R is methyl. This ester hydrolysis reaction can be carried out by treating said compound of the formula III or IV with water at a pH between 9 and 12, optionally in the presence of a co-solvent. In practice, it is conveniently carried out by treating the compound of formula III or IV with from about 1 to about 20 molar equivalents, and preferably about 2 to 5 molar equivalents, of an alkali metal hydroxide or alkaline earth metal hydroxide, in a mixture of water and a water-miscible, volatile, organic co-solvent. Typical co-solvents which can be used are lower-alkanols such as methanol and ethanol; glycols such as ethylene glycol and propylene glycol; and water-miscible, low-molecular weight ethers such as tetrahydrofuran and 1,2-dimethoxyethane. Usually, a large excess of water is used on molar basis, and sufficient co-solvent is added to give a homogeneous hydrolysis medium. Preferred basic agents for the hydrolysis reaction are the hydroxides of sodium and potassium.

Hydrolysis of an ester of formula III or IV is usually carried out at a temperature between 25° and 120° C., and preferably about 60° to 80° C. Reaction times vary according to a variety of factors, such as temperature and concentration of the reaction medium, but usually reaction times ranging from several hours (e.g. six hours) to several days (e.g. three days) are needed for the reaction to proceed substantially to completion.

At the end of the hydrolysis reaction, the organic co-solvent is usually removed by evaporation in vacuo, and the residual aqueous phase is extracted with a volatile, water-immiscible, organic solvent such as chloroform or dichloromethane. Evaporation of the organic extract then affords the required compound of formula I or II in the form of a carboxylate salt, where the cation corresponds to the alkali or alkaline earth metal used during the hydrolysis reaction. Alternatively, after removal of the organic co-solvent at the end of the hydrolysis reaction, the residual aqueous phase can be acidified (e.g. to a pH below about 3) before extraction with the water-immiscible, organic solvent. Evaporation of the extract then affords the compound I or II in the form of its free acid.

A compound of the formula I or II can be purified, if desired, by standard methods, such as recrystallization or chromatography.

An ester of the formula III or IV can be prepared by coupling a benzoate ester of the formula

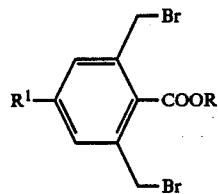 (V)

wherein R and $R^1$ are as defined previously, with a diol of the formula

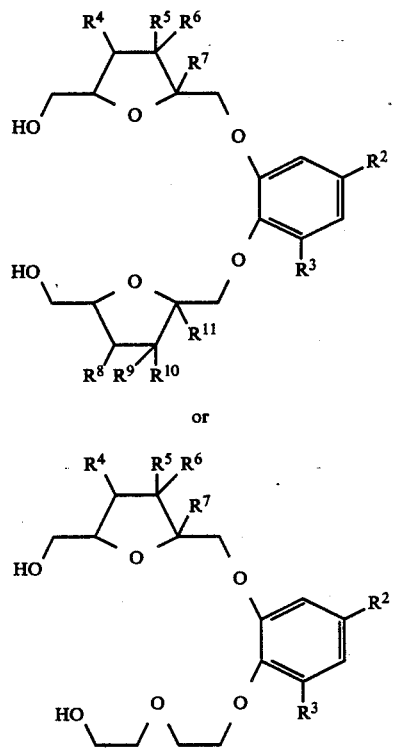

wherein $R^2$, $R^3$, $R^4$, $R^5$, $R^6$, $R^7$, $R^8$, $R^9$, $R^{10}$ and $R^{11}$ are as defined previously.

Coupling between a benzoate ester of the formula V and a diol of the formula VI or VII is usually achieved by contacting the reactants in a reaction-inert solvent in the presence of a strong, non-nucleophilic base. In a typical procedure, a tetrahydrofuran solution containing substantially equimolar amounts of a compound of the formula V and a diol of the formula VI or VII is added dropwise to a suspension of sodium hydride (2.2 molar equivalents) in refluxing tetrahydrofuran. The reaction mixture is then heated under reflux for a few hours, e.g. 2 to 10 hours, to complete the reaction. The excess of sodium hydride is decomposed by the careful addition of water (usually in the form of wet tetrahydrofuran) and the organic solvent is removed by evaporation in vacuo. The product is extracted into a volatile, water-immiscible organic solvent (e.g. dichloromethane) and removal of the solvent in vacuo then affords the crude product of formula III or IV. The crude product is usually purified by column chromatography on silica gel.

The diols of the formula VI, wherein $R^4$, $R^5$, $R^8$ and $R^9$ are each hydrogen or methyl, $R^6$, $R^7$, $R^{10}$ and $R^{11}$ are each hydrogen, and $R^2$ and $R^3$ are as defined previously, provided that $R^4$ and $R^8$ are the same and $R^5$ and $R^9$ are the same, can be prepared from the appropriate catechol of the formula IX using the method depicted in Scheme A.

SCHEME A

-continued
SCHEME A

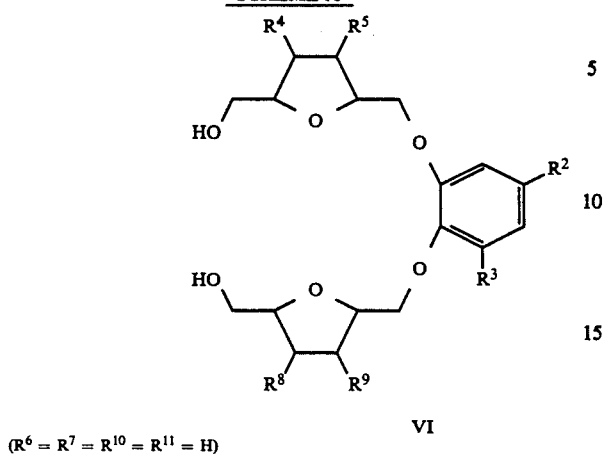

VI ($R^6 = R^7 = R^{10} = R^{11} = H$)

In the first step of Scheme A, the catechol of formula IX is dialkylated with a furan compound of the formula VIII, wherein R is a lower alkyl group (e.g. alkyl having 1 to 5 carbons) abd X is a leaving group such as chloro, bromo or iodo. Favorably R is methyl and X is chloro. This dialkylation is usually carried out by treating the catechol of formula IX with about 2.2 molar equivalents of the furan compound of formula VIII in the presence of an excess of potassium carbonate in a polar organic solvent, such as N,N-dimethylformamide, at about 140° C. for several hours. At the end of the reaction, the reaction mixture is diluted with water, and the compound of formula X (in which $R^4=R^8$ and $R^5=R^9$) can be recovered by extraction into a volatile, water-immiscible, organic solvent followed by evaporation of the solvent.

Step 2 of Scheme A involves hydrogenation of the furan rings in the compound of the formula X to give tetrahydrofuran rings, thereby producing the corresponding compound of the formula XI. This hydrogenation can be carried out by shaking or stirring a solution of the compound of the formula X in a reaction-inert solvent, such as a lower-alkanol (e.g. ethanol) or a low-molecular weight ester (e.g. ethyl acetate) under an atmosphere of hydrogen, at room temperature, for several hours, in the presence of a catalyst. An appropriate catalyst is 5% rhodium-on-alumina, and hydrogen pressures from about 5 to 15 kg/cm² are normally used. The compound of formula XI can be recovered by removal of the catalyst by filtration followed by removal of the solvent by evaporation.

Step 3 of Scheme A involves reduction of the RO—C(=O)— group in a compound of the formula XI to give the HO—CH₂— group, thereby producing the requisite compound of the formula VI. The reduction is conveniently carried out using an excess of lithium aluminum hydride, in an ether solvent such as tetrahydrofuran, at about room temperature, for several hours, according to standard procedures.

The diols of the formula VI, wherein $R^4$, $R^5$, $R^6$, $R^7$, $R^8$, $R^9$, $R^{10}$ and $R^{11}$ are each hydrogen or methyl, and $R^2$ and $R^3$ are as defined previously, provided that $R^4$ and $R^8$ are the same, $R^5$ and $R^9$ are the same, $R^6$ and $R^{10}$ are the same and $R^7$ and $R^{11}$ are the same, can be prepared from the appropriate catechol of the formula IX using the method depicted in Scheme B.

SCHEME B

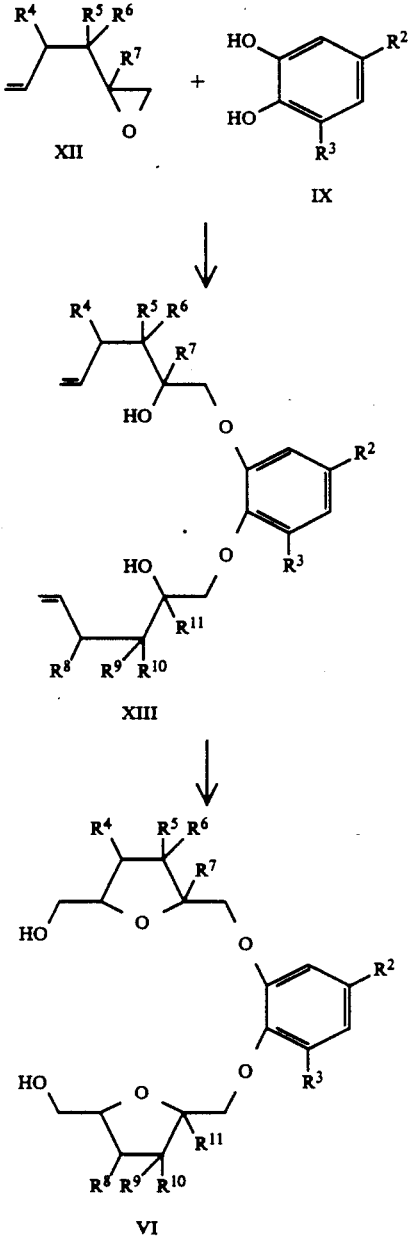

In the first step of Scheme B, the catechol of the formula IX is reacted with the appropriately substituted olefinic epoxide of the formula XII. This reaction is normally carried out by contacting the catechol with from about 2 to about 6 molar equivalents, and preferably from 3 to 4 molar equivalents, of the epoxide at elevated temperature, in the absence of a solvent. Temperatures in the range from 90° to 150° C., preferably 100° to 120° C., are normally used, and reaction times of several days are normally required. Additionally, it is often beneficial to add up to about one molar equivalent of a secondary or tertiary amine as a catalyst. Piperidine is commonly used as the amine catalyst. This affords the bis-olefin of the formula XIII in which $R^4$ and $R^8$ are the same, $R^5$ and $R^9$ are the same, $R^6$ and $R^{10}$ are the same and $R^7$ and $R^{11}$ are the same.

In the second step of Scheme B, the bis-olefin of the formula XIII is treated with an organic peroxycarboxylic acid. This effects epoxidation of the olefinic linkages, which is followed by opening of the epoxide rings and concomitant formation of tetrahydrofuran rings, to give the corresponding diol of formula VI. In a typical procedure, the bis-olefin of the formula XIII is reacted with from about 2 to about 5 molar equivalents, and preferably about 3 molar equivalents, of 3-chloroperbenzoic acid in a chlorinated hydrocarbon solvent, e.g. chloroform of dichloromethane, at room temperature for several hours, e.g. about 24 hours. The product of formula VI is isolated by standard methods, such as removal of the solvent by evaporation followed by chromatographic purification of the residue.

The diols of formula VII, wherein $R^2$, $R^3$, $R^4$, $R^5$, $R^6$ and $R^7$ are as defined previously, can be prepared from the appropriate catechol of the formula IX by the method depicted in Scheme C.

[2-tetrahydropyranyloxy]ethoxyl)ethyl chloride, the compound of the formula

(XVI)

wherein "THP" represents the 2-tetrahydropyranyl group, followed by removal of the THP protecting group. Both of these reactions are classical transformations which are carried out by standard methods. Alkylation of the phenol XIV is usually carried out by treatment with about one molar equivalent of the chloro compound in the presence of an excess of potassium carbonate in N,N-dimethylformamide solution at about 140° C. for several hours. At the end of the reaction the reaction mixture is diluted with water and the product can be recovered by extraction into a volatile, water-immiscible, organic solvent followed by evaporation of the solvent. The THP protecting group is removed by treatment with a catalytic amount of 1N hydrochloric acid in methanol solution at room temperature for several hours. Removal of the solvent by evaporation in

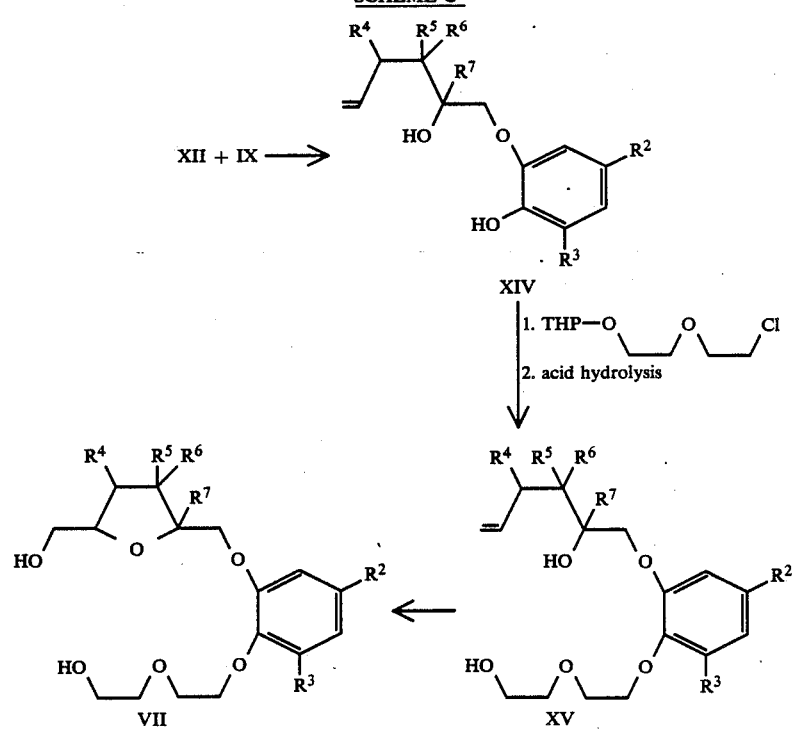

In the first step of Scheme C, the catechol of formula IX is reacted with the appropriate epoxide of the formula XII. This is carried out in the same manner described earlier for the first step of Scheme B, except that equimolar amounts of the catechol and epoxide are used. In practice, this leads to a mixture of products. However, the desired monoalkylated compound of the formula XIV can be isolated readily by standard separation techniques, e.g. by chromatography.

In the second step of Scheme C, the monoalkylated product of formula XIV is further alkylated with 2-(2- vacuo affords the olefin of the formula XV.

In the third step of Scheme C, the olefin of the formula XV is reacted with a peroxycarboxylic acid to give the requisite diol of the formula VII. This is carried out in exactly the same manner as described earlier for the second step of Scheme B, except that only one molar equivalent of peracid (e.g. 3-chloroperbenzoic acid) is used.

The diols of the formula VII, wherein $R^2$, $R^3$, $R^4$, $R^5$, $R^6$ and $R^7$ are as defined previously, can also be prepared by the method depicted in Scheme D.

SCHEME D

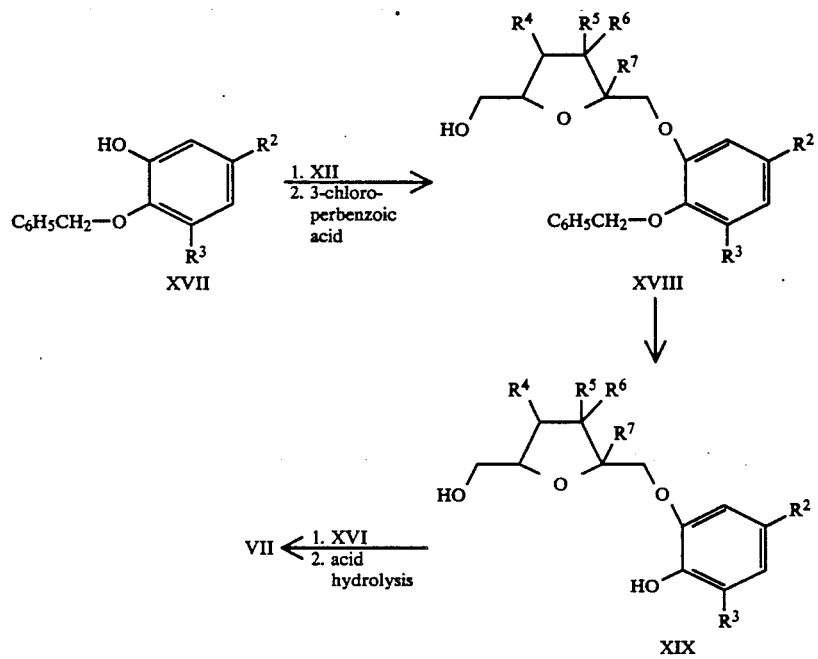

In Scheme D, the appropriate monobenzylated catechol of formula XVII is reacted with the requisite epoxide of the formula XII, followed by 3-chloroperbenzoic acid, to give the compound of the formula XVIII. These transformations are carried out in the same manner as described earlier for the two steps of Scheme B, except that equimolar amounts of the benzyl ether of formula XVII and epoxide of formula XII are used. The benzyl protecting group is then removed from the compound of formula XVIII by catalytic hydrogenolysis over a palladium-on-carbon catalyst, in ethanol solution, at a pressure of from about 4 to 10 kg/cm². This affords the phenol of formula XIX. Alkylation of the latter phenol with the chloro compound of the formula XVI, followed by removal of the THP protecting group using dilute hydrochloric acid in methanol, affords the required diol of the formula VII. Alkylation of the phenol of the formula XIX and removal of the THP group are carried out as described earlier for conversion of the phenol of formula XIV into the compound of the formula XV.

The diols of the formula VII, wherein $R^2$, $R^3$, $R^4$, $R^5$ and $R^6$ are as defined previously, can also be prepared by the method depicted in Scheme E.

SCHEME E

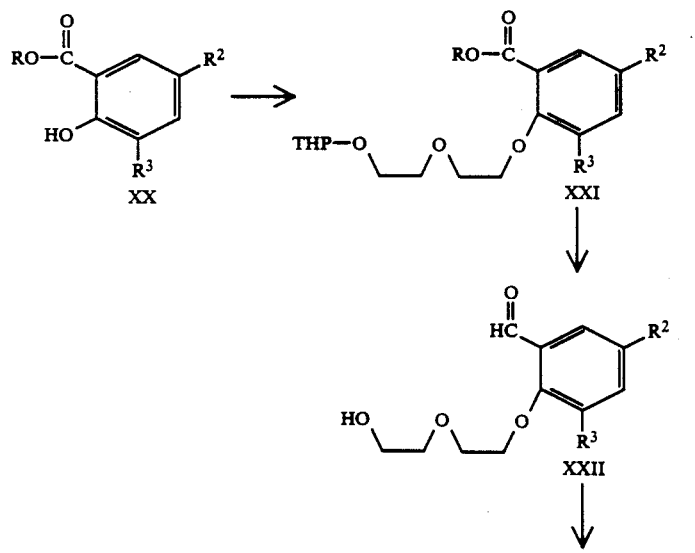

SCHEME E
-continued

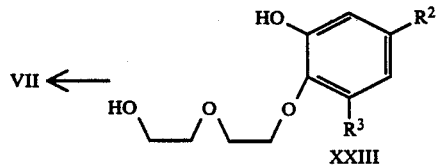

In the first step of Scheme E, the appropriate salicylate ester of the formula XX, wherein R is a lower-alkyl group (e.g. alkyl having 1 to 5 carbons, particularly methyl), is alkylated with the chloro compound of the formula XVI to give the compound of the formula XXI, as described previously for alkylation of the phenol of the formula XIV.

In the second step of Scheme E, the salicylate ester of the formula XXI is reduced with lithium aluminum hydride to give the corresponding benzyl alcohol, which is then oxidized to the corresponding benzaldehyde (e.g. using pyridinium dichromate in dichloromethane). Finally the THP-protecting group is removed by hydrolysis with dilute hydrochloric acid in methanol by the method described previously to give the hydroxy-aldehyde of formula XXII.

In the third step of Scheme E, the hydroxy-aldehyde of the formula XXII is subjected to Baeyer-Villiger oxidation, followed by hydrolysis (preferably acid-catalyzed hydrolysis), both according to standard procedures, to give the phenol of the formula XXIII.

Finally, in the fourth step of Scheme E, the phenol of the formula XXIII is reacted with an epoxide of the formula XII, followed by 3-chloroperbenzoic acid, to give the requisite diol of the formula VII. These latter transformations are carried out in the same manner as described earlier for the two steps of Scheme B, except that equimolar amounts of the phenol of the formula XXIII and the epoxide of the formula XII are used.

The intermediates of the formula XIX can be used to prepare diols of the formula VI, wherein $R^2$ to $R^{11}$ are as defined previously but in which, if desired, $R^4$ and $R^8$ can be different, $R^5$ and $R^9$ can be different, $R^6$ and $R^{10}$ can be different and $R^7$ and $R^{11}$ can be different. Thus, the intermediate of the formula XIX is reacted with an epoxide of the formula XII followed by treatment with 3-chloroperbenzoic acid, in the same manner as described earlier for the two steps of Scheme B, except that equimolar amounts of the phenol of the formula XIX and the epoxide of the formula XII are used.

The salicylate esters of the formula XX, wherein R is as defined previously, can also be used to prepare diols of the formula VI, wherein $R^2$ to $R^{11}$ are as defined previously but in which, if desired, $R^4$ and $R^8$ can be different, $R^5$ and $R^9$ can be different, $R^6$ and $R^{10}$ can be different and $R^7$ and $R^{11}$ can be different. Firstly, the salicylate ester of the formula XX is reacted with an epoxide of the formula XII, followed by 3-chloroperbenzoic acid, using methodology previously described; secondly, the RO—C(=O)— group is converted into a phenolic hydroxy group by reduction with lithium aluminum hydride, oxidation to the benzaldehyde (e.g. with $MNO_2$), Baeyer-Villiger oxidation and acid hydrolysis, in a manner analogous to that described for Scheme E for these transformations; and, thirdly, the phenol thus obtained is reacted with an epoxide of the formula XII, followed by 3-chloroperbenzoic acid, also using the methodology previously described. This sequence is shown in Scheme F.

SCHEME F

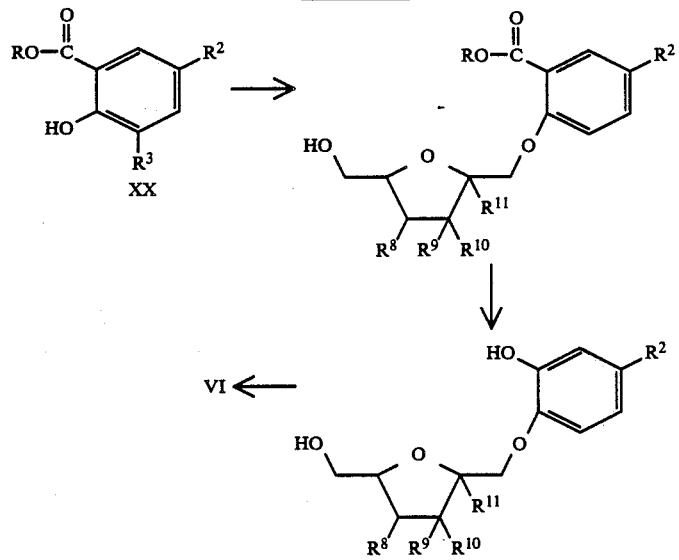

Many of the simple catechols of the formula IX are known compounds, which can be prepared by the known methods, or they are analogs of known compounds, which can be prepared by analogous procedures. Thus, the $R^2$ substituent can often be introduced into a catechol of the formula

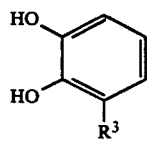
(XXIV)

or its dimethyl ether, wherein $R^3$ is hydrogen or alkyl having 1 to 8 carbons, by acid-catalyzed reaction with an olefin or an alcohol, or by Friedel-Crafts alkylation using an alkyl halide, followed, if necessary by demethylation, e.g.

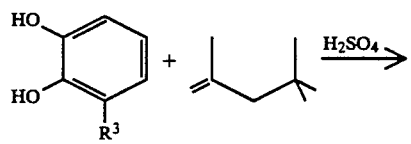

See further J. Jelinek, Chem. Primsyl, 9, 398 (1959); Chem. Abs., 54, 86911 (1960).

Additionally, catechols of the formula XXIV can be reacted with an alkanoyl chloride to give a diester of the formula XXV, which on heating with a Lewis acid (e.g. aluminum chloride) in carbon disulfide undergoes the Fries rearrangement to give an acyl derivative of the formula XXVI, viz:

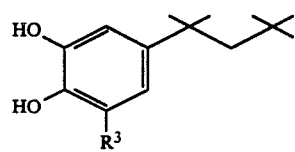

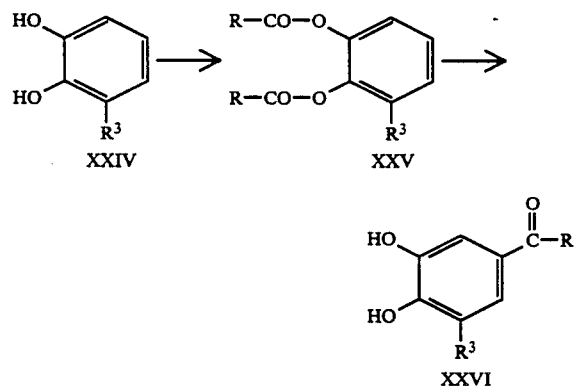

wherein R is a lower-alkyl group. The —C(=O)—R group in a compound of the formula XXVI can be transformed into various $R^2$ substitutents by conventional methods, well-known to those skilled in the art.

Catechols of the formula IX, wherein $R^3$ is thiophenoxymethyl can be prepared from the appropriate catechol of the formula XXX by a Mannich reaction with paraformaldehyde, followed by reaction with thiophenol;

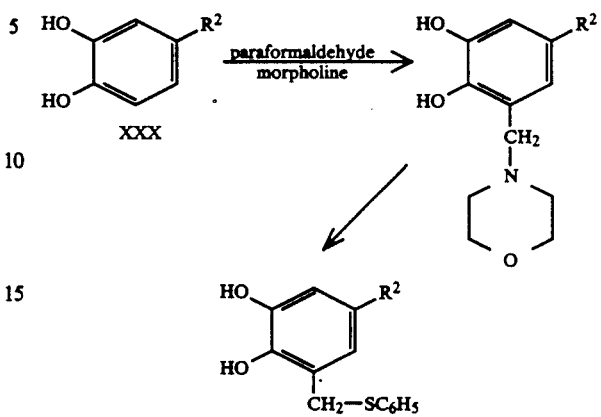

The Mannich reaction can be carried out be standard methods; see further Fields et al., Journal of Organic Chemistry, 29, 2640 (1964). Reaction of the Mannich base with thiophenol can be carried out by heating the reactants in a polar organic solvent, such as N,N-dimethylformamide, for several hours at about 80° to 140° C.

The compounds of the formula XVII can be prepared from the appropriate salicylate ester of the formula XX as follows:

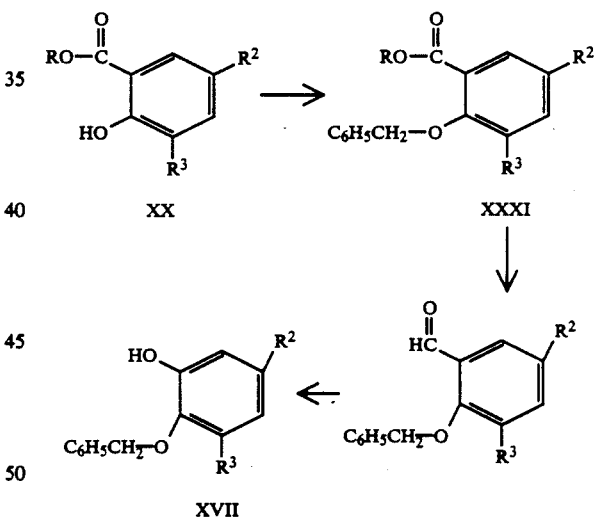

wherein R is a lower-alkyl group and $R^2$ and $R^3$ are as defined previously. Conversion of the RO—C(=O)— group in the compound of formula XXXI into an aldehyde function and thence to a phenolic hydroxy group is achieved by reduction with lithium aluminum hydride, followed by oxidation with pyridinium dichromate, followed by Baeyer-Villiger oxidation, followed by acid-catalyzed hydrolysis, in a manner analogous to that described for Scheme E.

The compounds of formulae I and II, in which $R^3$ is thiophenoxymethyl, can be prepared from the corresponding diol of formula VI or VII, in which $R^3$ is thiophenoxymethyl. These latter diols are conveniently prepared from intermediates of the formula XXXII, which are prepared from a compound of the formula XIX in which $R^3$ is hydrogen, as follows:

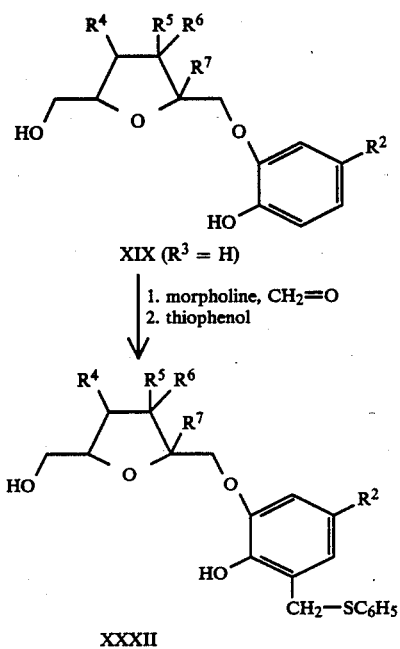

Conversion of XIX ($R^3$=H) into XXXII can be carried out using a Mannich reaction, followed by reaction with thiophenol, as described earlier for a catechol of formula XXX. A compound of the formula XXXII can be converted into a diol of the formula VI or VII by attachment of the appropriate side-chain to the phenolic hydroxy group by methods previously described. (See Schemes D and E.)

The compounds of the formula V can be prepared by bromination of the corresponding 2,6-dimethylbenzoate ester of the formula XXXIII:

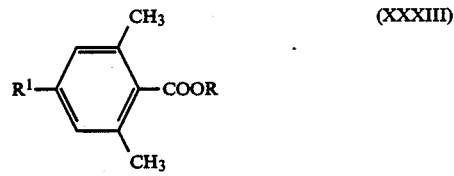

wherein R and $R^1$ are as defined previously. The bromination can be carried out using standard procedures. A convenient method involves bromination with N-bromosuccinimide or N,N-dibromo-5,5-dimethylhydantoin in refluxing carbon tetrachloride with irradiation from a sunlamp. The crude products can be recrystallized from a non-polar solvent, such as petroleum ether or cyclohexane.

The 2,6-dimethylbenzoate esters of the formula XXXIII are prepared by known methods or methods analogous to known methods. See further: M. L. Bender and M. C. Chen, *Journal of the American Chemical Society*, 85, 30 (1963); *ibid*, 85, 37 (1963).

The compounds of the formulae I and II are acidic and they will form carboxylate salts. All such salts are within the scope of this invention, and they can be prepared by conventional methods for lipophilic carboxylic acids. For example, they can be prepared by contacting the carboxylic acid with a stoichiometric equivalent of an appropriate basic agent, in a nonaqueous or partially aqueous solvent. They can be recovered by solvent evaporation, by filtration, or by precipitation using a non-solvent followed by filtration, as appropriate. Typical salts of the compounds of formulae I and II which can be prepared include primary, secondary and tertiary amine salts, as well as alkali metal and alkaline earth metal salts. Especially favorable are sodium and potassium salts.

In a particularly convenient method of preparing salts of the compounds of formulae I and II, a solution of the compound of formula I or II in a volatile, water immiscible, organic solvent is washed with an aqueous solution containing at least a stoichiometric equivalent, and preferably a large excess, of an appropriate basic agent. After drying the organic solvent solution, it is evaporated in vacuo to give the desired salt. Typical basic agents which can be used for this purpose include alkali metal hydroxides, such as sodium hydroxide and potassium hydroxide, alkaline earth metal hydroxides, such as calcium hydroxide and barium hydroxide, and ammonium hydroxide.

As indicated hereinbefore, the compounds of formulae I and II, and the salts thereof, are useful for increasing the efficiency of feed utilization in ruminant animals, i.e. animals which have multiple stomachs, one of which is a rumen. In particular, the compounds of formulae I and II are useful in cattle and sheep. For the purpose of increasing food utilization, a compound of formula I or II is administered orally to a ruminant, on a daily basis, and in an amount which is effective in increasing propionate formation in the animal's rumen. The compound of formula I or II can be administered orally by a variety of methods, in accordance with standard practices in veterinary science and animal husbandry. However, a convenient method of administering a compound of formula I or II is to blend the compound of formula I or II with the animal's food, at such a level that the animal receives an effective propionate-increasing amount.

British Pat. No. 1,197,826 describes a method for measuring the ability of compounds to increase propionate formation in the rumen of ruminant animals. The test method involves the use of an apparatus in which the digestive processes of the ruminants are conducted and studied in vitro. The animal feed, a sample of rumen contents and the compound under study are introduced into and withdrawn from a laboratory unit under carefully controlled conditions and the changes taking place are studied critically and progressively during the consumption of the feed by the microbial flora in the rumen contents. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid.

Thus, rumen fluid is collected from a fistulated cow which is fed on a commerical fattening ration plus hay.

The rumen fluid is immediately filtered through cheese cloth, and 10 ml added to a 50 ml conical flask containing 400 mg of standard substrate (68% corn starch+17% cellulose+15% extracted soybean meal), 10 ml of a pH 6.8 buffer and the test compound. The flasks are gassed with oxygen free nitrogen for about 2 minutes and incubated in a shaking water bath at 39° C. for about 16 hours. All tests are conducted in triplicate. After incubation, 5 ml of the sample are mixed with 1 ml of 25% metaphosphoric acid. After 10 minutes, 0.25 ml of formic acid is added and the mixture centrifuged at 1500 r.p.m. for 10 minutes. Samples are then analyzed by gas-liquid chromatography by the method of D. W. Kellog in J. *Dairy Science*, 52, 1690 (1969). Peak heights for acetic, propionic and butyric acids are determined for samples from untreated and treated incubation flasks.

Thus, the amount of compound I or II which must be administered to a ruminant animal to increase feed utilization efficiency depends on the ability of the compound to increase propionate production in the rumen. However, a compound of formula I or II will normally be administered orally to a ruminant at a dosage in the range from 0.5 to 50 mg/kg of body weight per day.

In addition to their ability to increase feed utilization in ruminants, the compounds of formulae I and II are active as antibacterial agents in vitro. This makes them useful for a variety of sanitary purposes, such as sterilization of hospital surfaces, and as preservatives, e.g., paint preservatives.

The antibacterial activity of a compound of the formula I or II can be demonstrated by measuring the minimum inhibitory concentration (MIC) against a variety of organisms, according to standard procedures. Thus, the MIC's can be measured by the procedure recommeded by the International Collaborative Study on Antibiotic Sensitivity Testing (Ericcson and Sherris, *Acta. Pathologica et Microbiologia Scandinav*, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Typical microorganisms against which the compounds of formulae I and II are active in vitro are Staphylococcus aureus, Streptococcus equi and Clostridium perfringens.

The following examples and preparations are being provided for the purpose of further illustration. Infrared (IR) spectra were measured as neat liquids, potassium bromide disks or dichloromethane solutions, and positions of significant absorption peaks are given in reciprocal centimeters ($cm^{-1}$). Nuclear magnetic resonance (NMR) spectra were measured as solutions in deuterochloroform ($CDCl_3$) at 60 MHz, and peak positions are given in parts per million (ppm) downfield from internal tetramethylsilane. The following abbreviations for peak shapes are used: s, singlet; bs, broad singlet; d, doublet; t, triplet; q, quartet; m, multiplet. For low-resolution mass spectra (MS) and high-resolution mass spectra (HRMS), peaks are given as mass-to-charge (m/e) ratios.

EXAMPLE 1

COMPOUND I ($R^1$ is t-butyl; $R^2$ is t-octyl; $R^3$, $R^4$, $R^5$, $R^6$, $R^7$, $R^8$, $R^9$, $R^{10}$ and $R^{11}$ are hydrogen)

A mixture of 2.9 g (4.4 mmole) of the methyl ester of the title compound, 150 ml of 5% potassium hydroxide and 100 ml of ethanol was heated under reflux for 18 hours, and then the ethanol was removed by evaporation in vacuo. The residual aqueous phase was extracted with chloroform, and the extracts were washed with water, followed by saturated sodium chloride solution, and then dried ($MgSO_4$). Evaporation of the solvent followed by drying the residue under high vacuum gave 2.45 g (82% yield) of the title compound as its potassium salt.

IR ($CHCl_3$): 1600 $cm^{-1}$.

NMR ($CDCl_3$): 7.3 (s, 2H), 6.9 (m, 3H ), 4.7 (s, 4H), 4.4–3.3 (m, 13H), 2.0–1.6 (m, 10H), 1.3 (s, 15H), 0.7 (s, 9H) ppm.

HRMS (on free acid): M+ =652.3936.

$C_{39}H_{56}O_8$ requires 652.3975.

EXAMPLE 2

The compounds in Tables I and II were prepared by hydrolysis of the corresponding methyl ester, using the procedure of Example I. The free acid form of the compounds was obtained by dissolving the potassium salt in chloroform, washing the chloroform solution with dilute hydrochloric acid and evaporating the dried chloroform solution.

TABLE I

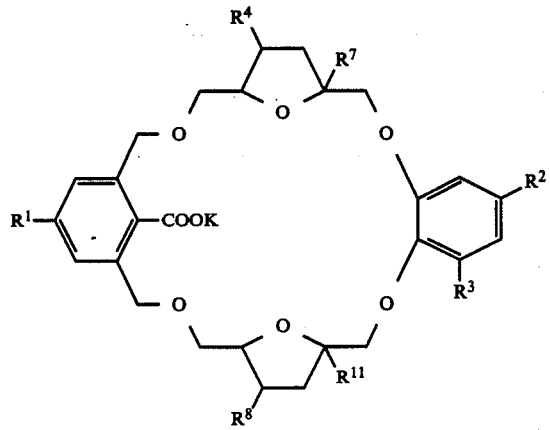

| R[1] | R[2] | R[3] | R[4] | R[7] | R[8] | R[11] | Yield (%) | Spectral Data |
|---|---|---|---|---|---|---|---|---|
| H | H | H | H | H | H | H | 50 | IR(KBr): 3484, 2941, 1610. NMR(CDCl$_3$): 7.2 (s, 3H), 6.8 (s, 4H), 4.7 (s, 4H), 4.3–3.2 (m, 12H), 2.1–1.2 (m, 8H). HRMS[1]: 484.2092. |
| H | t-butyl | H | H | H | H | H | 63 | IR(KBr): 2994, 1730. NMR(CDCl$_3$): 7.2 (s, 3H), 6.8 (m, 3H), 4.6 (s, 4H), 4.4–4.0 (m, 8H), 3.8–3.5 (m, 4H), 2.0 (m, 8H), 1.4 (s, 9H). MS: 540. |
| H | t-octyl | H | H | H | H | H | 75 | IR(CH$_2$Cl$_2$): 1600. NMR[1](CDCl$_3$): 7.2 (s, 3H), 6.8 (m, 3H), 4.6 (s, 4H), 4.7–3.8 (m, 8H), 3.6–3.4 (m, 4H), 1.9 (m, 10H), 1.3 (s, 6H), 0.8 (s, 9H). |
| t-butyl | t-butyl | H | H | H | H | H | 70 | IR(CHCl$_3$): 1600. NMR[1](CDCl$_3$): 7.3 (s, 2H), 6.8 (m, 3H), 4.7 (s, 4H), 4.5–3.9 (m, 8H), 3.7–3.4 (m, 4H), 1.9 (m, 8H), 1.3 (d, 18H). HRMS: 596.3523. |
| t-butyl | t-octyl | H | H | H | H | H | 45 | IR(CH$_2$Cl$_2$): 1600. NMR[1](CDCl$_3$): 7.3 (s, 2H), 6.7 (m, 3H), 4.6 (s, 4H), 4.4–3.7 (m, 8H), 3.6–3.2 (m, 4H), 1.9 (m, 8H), 1.4 (m, 15H), 1.0 (s, 9H). |
| t-butyl | t-octyl | methyl | H | H | H | H | 32 | IR(CH$_2$Cl$_2$): 1590. NMR(CDCl$_3$): 7.3 (m, 2H), 6.7 (s, 2H), 4.7 (d, 4H), 4.5–3.2 (m, 12H), 2.2 (s, 3H), 2.0–1.5 (m, 10H), 1.3 (d, 15H), 0.9 (s, 9H). MS[1]: 666. |
| t-butyl | t-octyl | H | CH$_3$ | H | CH$_3$ | H | 80 | IR(CH$_2$Cl$_2$): 1600. NMR(CDCl$_3$): 7.3 (s, 2H), 6.8 (m, 3H), 4.8–3.8 (m, 12H), 3.7–3.4 (m, 4H), 2.7–1.9 (m, 6H), 1.8 (s, 2H), 1.4 (s, 15H), 1.1 (d, 6H), 0.8 (s, 9H). |
| H | t-octyl | H | CH$_3$ | H | CH$_3$ | H | 85 | IR(CH$_2$Cl$_2$): 1605. |
| t-butyl | t-butyl | H | H | CH$_3$ | H | CH$_3$ | 62 | IR[1](CH$_2$Cl$_2$): 3600–2600, 1725. NMR[1](CDCl$_3$): 7.9 (s, 1H), 7.2 (m, 2H), 6.8 (m, 3H), 4.6 (s, 4H), 4.4–3.3 (m, 10H), 1.9 (m, 8H), 1.3 (bs, 24H). |
| H | t-butyl | H | H | CH$_3$ | H | CH$_3$ | 94 | IR(CH$_2$Cl$_2$): 1600. NMR(CDCl$_3$): 7.2 (m, 3H), 6.9 (m, 3H), 4.8–3.2 (m, 14H), 2.3–1.6 (m, 8H), 1.4 (bs, 15H). |
| t-butyl | t-octyl | H | H | CH$_3$ | H | CH$_3$ | 77 | IR(CH$_2$Cl$_2$): 1600. NMR(CDCl$_3$): 7.3 (m, 2H), 6.9 (m, 3H), 4.8–3.2 (m, 14H), 2.2–1.6 (m, 10H), 1.3 (m, 21H), 0.7 (s, 9H). |
| H | t-octyl | H | H | CH$_3$ | H | CH$_3$ | 42 | IR(CH$_2$Cl$_2$): 1590. NMR(CDCl$_3$): 7.2 (m, 3H), 6.8 |

TABLE I-continued

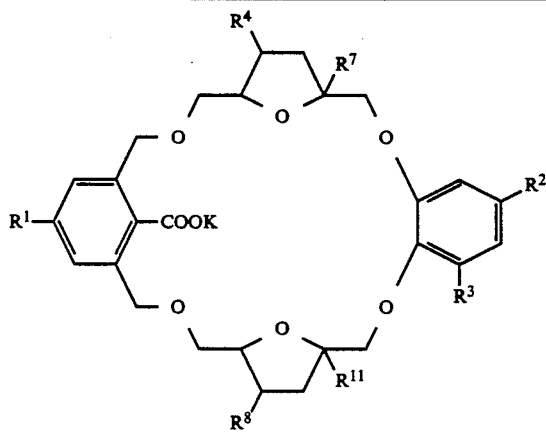

| R¹ | R² | R³ | R⁴ | R⁷ | R⁸ | R¹¹ | Yield (%) | Spectral Data |
|---|---|---|---|---|---|---|---|---|
| t-butyl | phenyl | H | H | CH₃ | H | CH₃ | 25 | (m, 3H), 4.6 (m, 4H), 4.5–3.3 (m, 10H), 1.8 (m, 10H), 1.4 (m, 12H), 0.8 (s, 9H).<br>IR(CH₂Cl₂): 1600. |
| H | phenyl | H | H | CH₃ | H | CH₃ | 73 | NMR(CDCl₃): 7.5–6.7 (m, 10H), 4.8–3.2 (m, 14H), 1.7 (m, 8H), 1.3 (m, 15H).<br>IR(CH₂Cl₂): 1600. |
| t-butyl | t-octyl | methyl | H | CH₃ | H | CH₃ | 50 | IR(CH₂Cl₂): 1600. |

¹spectrum measured on the free acid.

TABLE II

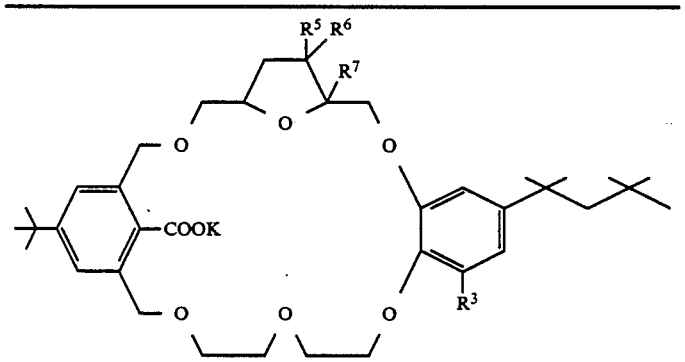

| R³ | R⁵ | R⁶ | R⁷ | Yield (%) | Spectral Data |
|---|---|---|---|---|---|
| methyl | H | H | CH₃ | 80 | IR(KBr): 3427, 2947, 1729, 1607, 1588. |
| hydrogen | H | H | CH₃ | 65 | IR(CH₂Cl₂): 1590. |
| thiophenoxymethyl | H | H | CH₃ | 77 | IR(KBr): 1588. |
| methyl | CH₃ | CH₃ | H | 50 | IR(KBr): 3426, 2947, 2898, 1587.<br>NMR(CDCl₃): 7.2 (m, 2H), 6.7 (m, 2H), 4.6 (m, 4H), 4.3–3.3 (m, 14H), 2.2 (s, 3H), 2.0 (m, 2H), 1.3 (s, 15H), 1.0 (m, 6H), 0.7 (s, 9H). |
| hydrogen | CH₃ | CH₃ | H | 65 | IR(KBr): 3390, 2907, 1605, 1582. |

EXAMPLE 3

The compounds in Tables III and IV can be prepared by reaction of the appropriate diol of the formula VI or VII with methyl 2,6-di(bromomethyl)-4-t-butylbenzoate and sodium hydride according to the procedure of Preparation 5, followed by hydrolysis of the macrocyclic ester thus obtained according to the procedure of Example 1.

TABLE III

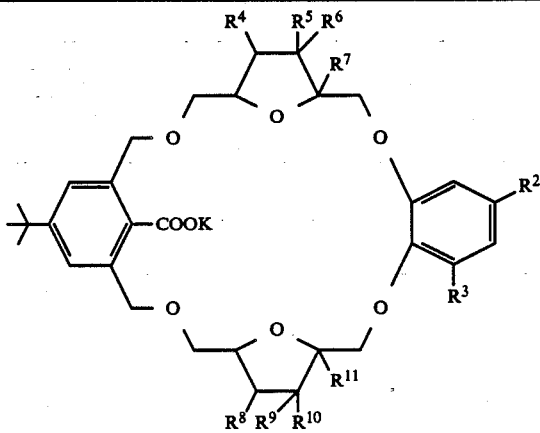

| R² | R³ | R⁴ | R⁵ | R⁶ | R⁷ | R⁸ | R⁹ | R¹⁰ | R¹¹ |
|---|---|---|---|---|---|---|---|---|---|
| methyl | n-octyl | H | CH₃ | H | H | CH₃ | H | H | H |
| t-octyl | ethyl | CH₃ | H | H | H | H | H | H | H |
| ethyl | isobutyl | H | H | H | H | CH₃ | H | H | H |
| t-octyl | n-hexyl | H | H | H | H | H | H | H | H |
| n-pentyl | hydrogen | H | CH₃ | CH₃ | H | H | CH₃ | CH₃ | H |
| phenyl | isopropyl | CH₃ | CH₃ | H | H | CH₃ | CH₃ | H | H |
| n-octyl | thiophenoxymethyl | H | H | H | H | H | H | H | H |
| n-decyl | hydrogen | H | H | H | CH₃ | H | H | H | CH₃ |
| t-octyl | methyl | H | H | H | H | CH₃ | CH₃ | H | H |
| hydrogen | n-octyl | H | H | H | H | H | H | H | H |

TABLE IV

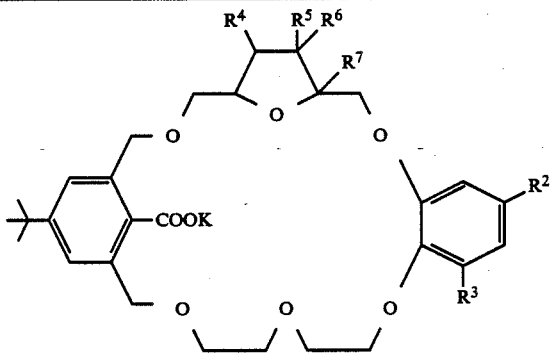

| R² | R³ | R⁴ | R⁵ | R⁶ | R⁷ |
|---|---|---|---|---|---|
| hydrogen | n-octyl | H | H | H | H |
| methyl | n-hexyl | CH₃ | CH₃ | H | H |
| t-octyl | hydrogen | CH₃ | H | H | H |
| ethyl | n-octyl | H | CH₃ | H | H |
| isobutyl | isopropyl | H | H | H | H |
| phenyl | ethyl | H | H | H | CH₃ |
| hydrogen | methyl | H | CH₃ | CH₃ | H |
| t-octyl | thiophenoxymethyl | H | H | H | H |
| n-decyl | hydrogen | H | H | H | H |

EXAMPLE 4

1,2-Di(5-hydroxymethyl-2-tetrahydrofuranylmethoxy)-4-t-octylbenzene

A solution of the product of Preparation 3 (4.8 g, 9.5 mmole) in dry tetrahydrofuran was added dropwise to a slurry of 1.1 g (29 mmole) of lithium aluminum hydride in 150 ml of tetrahydrofuran at 0° C. After the addition was complete, the reaction mixture was stirred at room temperature for 48 hours. A solution of 2 ml of water in 25 ml of tetrahydrofuran was then added, slowly and cautiously, followed by 5 ml of saturated aqueous sodium sulfate. The resulting mixture was filtered and the filtrate was evaporated in vacuo. The residual oil was dissolved in chloroform, and the chloroform solution was then dried (MgSO₄) and evaporated. This produced an oil which was purified by column chromatography using silica gel, to give 2.7 g of the title diol as a colorless oil.

NMR(CDCl₃): 6.9 (m, 3H), 4.4–3.4 (m, 12H), 2.0 (m, 8H), 1.7 (s, 2H), 1.4 (s, 6H), 0.8 (s, 9H) ppm.

EXAMPLE 5

The products of Preparation 4 were reduced with lithium aluminum hydride, using the procedure of Example 4, to give the diols in Table V as oils.

TABLE V

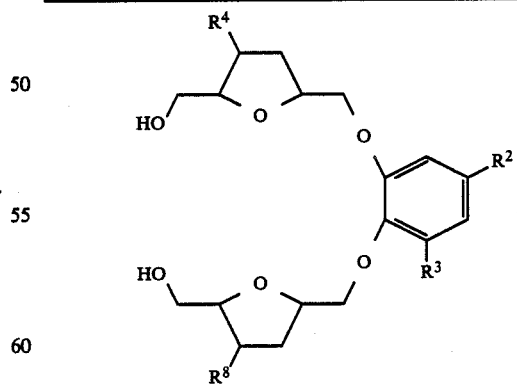

| R² | R³ | R⁴ | R⁸ | Yield (%) | Spectral Data |
|---|---|---|---|---|---|
| hydrogen | hydrogen | H | H | 77 | NMR(CDCl₃): 6.9(s, 4H), 4.4–3.4(m, 12H), 3.3 (s, 2H), 1.9 (m, 8H). |
| t-butyl | hydrogen | H | H | 95 | NMR(CDCl₃): 6.9 (m, |

TABLE V-continued

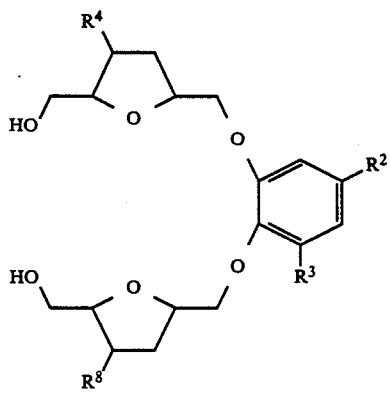

| R[2] | R[3] | R[4] | R[8] | Yield (%) | Spectral Data |
|---|---|---|---|---|---|
| | | | | | 3H), 4.5-3.8 (m, 8H, 3.8-3.5 (m, 4H), 2.0 (m, 8H), 1.4 (s, 9H). |
| n-octyl | hydrogen | H | H | 45 | NMR(CDCl$_3$): 6.7 (s, 3H), 4.4-3.8 (m, 8H), 3.7-3.5 (m, 4H), 3.3 (s, 2H), 2.5 (m, 2H), 2.0 (m, 8H), 1.3 (m, 12H), 0.9 (m, 3H). |
| t-octyl | methyl | H | H | 26 | NMR(CDCl$_3$): 6.7 (s, 2H), 4.5-3.9 (m, 8H), 3.5 (m, 4H), 3.4 (s, 2H), 2.3 (s, 3H), 2.0 (m, 8H), 1.7 (s, 2H), 1.4 (s, 6H), 0.8 (s, 9H). |
| t-octyl | hydrogen | CH$_3$ | CH$_3$ | 23 | NMR(CDCl$_3$): 6.8 (m, 3H), 4.5-3.8 (m, 8H), 3.8-3.6 (m, 4H), 3.2 (s, 2H), 2.8-1.7 (m, 8H), 1.4 (s, 6H), 1.2 (d, 6H), 0.8 (s, 9H). |

EXAMPLE 6

1,2-Di(5-Hydroxymethyl-2-methyl-2-tetrahydrofuranylmethoxy)-4-t-butylbenzene

To a solution of the product of Preparation 7 (2.77 g, 7.1 mmole) in 250 ml of dichloromethane was added dropwise, with stirring, a solution of 3.6 g (20.9 mmole) of 3-chloroperbenzoic acid in 150 ml of dichloromethane. Stirring was continued for 20 hours at room temperature, and then the reaction mixture was washed with 5% potassium hydroxide solution, followed by water. The resulting solution was dried (MgSO$_4$) and evaporated in vacuo, and the residue was purified by column chromatography on silica gel, eluting with ethyl acetate-chloroform (1:1). This afforded 2.1 g of the title compound (70% yield) as an oil.

NMR(CDCl$_3$): 6.9 (m, 3H), 4.4-3.4 (m, 10H), 3.2 (s, 2H), 1.9 (m, 8H), 1.3 (bs, 15H) ppm.

HRMS: M+ =442.2707.

EXAMPLE 7

Reaction of the appropriate catechol with 1,2-epoxy-2-methyl-5-hexene according to the procedure of Preparation 7, followed by oxidation with 3-chloroperbenzoic acid according to the procedure of Example 6, afforded the compounds in Table VI as oils.

TABLE VI

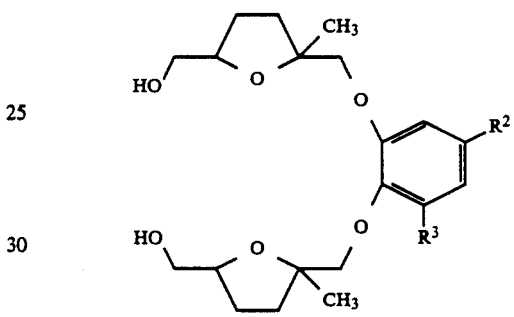

| R[2] | R[3] | Yield[1] (%) | Yield[2] (%) | Spectral Data |
|---|---|---|---|---|
| t-octyl | hydrogen | 89 | 42 | NMR(CDCl$_3$): 6.9 (m, 3H), 4.4-3.4 (m, 10H), 2.8 (s, 2H), 2.0 (m, 8H), 1.7 (s, 2H), 1.4 (d, 12H), 0.8 (s, 9H). |
| phenyl | hydrogen | 76 | 50 | NMR(CDCl$_3$): 7.6-6.9 (m, 8H), 4.3-3.4 (m, 10H), 2.8 (s, 2H), 2.2-1.7 (m, 8H), 1.4 (m, 6H). |
| t-octyl | methyl | 34 | 25 | NMR(CDCl$_3$): 6.8 (s, 2H), 4.2-3.5 (m, 10H), 2.4-1.7 (m, 13H), 1.3 (m, 12H), 0.9 (s, 9H). |

[1]for catechol-epoxide reaction
[2]for 3-chloroperbenzoic acid reaction

EXAMPLE 8

The diols in Table VII can be prepared by reaction of the appropriate catechol of the formula IX with the requisite epoxide of the formula XII according to the procedure of Preparation 7, followed by oxidation with 3-chloroperbenzoic acid according to the procedure of Example 6.

TABLE VII

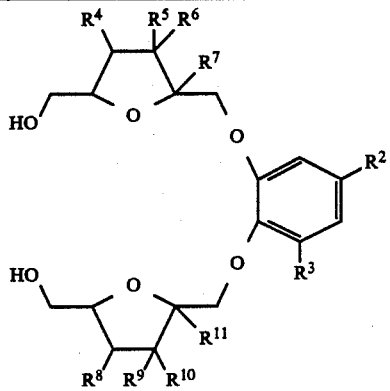

| R² | R³ | R⁴ | R⁵ | R⁶ | R⁷ | R⁸ | R⁹ | R¹⁰ | R¹¹ |
|---|---|---|---|---|---|---|---|---|---|
| t-octyl | n-hexyl | H | H | H | H | H | H | H | H |
| n-pentyl | hydrogen | H | CH₃ | CH₃ | H | H | CH₃ | CH₃ | H |
| phenyl | isopropyl | CH₃ | CH₃ | H | H | CH₃ | CH₃ | H | H |
| n-octyl | thiophenoxymethyl | H | H | H | H | H | H | H | H |
| n-decyl | hydrogen | H | H | H | CH₃ | H | H | H | CH₃ |
| hydrogen | n-octyl | H | H | H | H | H | H | H | H |

EXAMPLE 9

1-(2-[2-Hydroxyethoxy]ethoxy)-2-(5-hydroxymethyl-2-methyl-2-tetrahydrofuranylmethoxy)-6-methyl-4-t-octylbenzene To a solution of the product of Preparation 11 (1 g, 2.6 mmole) in 20 ml of dichloromethane was added a solution of 0.64 g (3.2 mmole) of 3-chloroperbenzoic acid in 10 ml of dichloromethane, with stirring. Stirring was continued for 16 hours and then the reaction mixture was washed with saturated sodium bisulfite solution, followed by water, followed by saturated sodium carbonate. The resulting dichloromethane solution was dried (MgSO₄) and evaporated in vacuo to give 0.95 g of crude product as an oil which was used without further purification.

NMR(CDCl₃): 6.8 (s, 2H), 4.3–3.5 (m, 15H), 2.3 (s, 3H), 2.1–1.6 (m, 6H), 1.4 (d, 9H), 0.8 (s, 9H) ppm.

EXAMPLE 10

Reaction of the appropriate olefin with 3-chloroperbenzoic acid, using the procedure of Example 9, afforded the following diols:

1-(2-[2-hydroxyethoxy]ethoxy)-2(5-hydroxymethyl-2-methyl-2-tetrahydrofuranylmethoxy)-4-t-octylbenzene; oil; 55% yield; NMR(CDCl₃): 6.8 (m, 3H), 4.3–3.5 (m, 15H), 2.2–1.6 (m, 6H), 1.4 (m, 9H), 0.8 (s, 9H) ppm.

1-(2-[2-hydroxyethoxy]ethoxy)-2-(5-hydroxymethyl-3,3-dimethyl-2-tetrahydrofuranylmethoxy)-6-methyl-4-t-octylbenzene; oil; 50% yield; NMR(CDCl₃): 6.8 (m, 2H), 4.4–3.6 (m, 14H), 2.3 (s, 3H), 1.7 (m, 4H), 1.4 (s, 6H), 1.0 (s, 6H), 0.8 (s, 9H) ppm.

1-(2-[hydroxyethoxy]ethoxy)-2-(5-hydroxymethyl-3,3-dimethyl-2-tetrahydrofuranylmethoxy)-4-t-octylbenzene; oil; 82% yield; NMR(CDCl₃): 6.9 (m, 3H), 4.4–3.4 (m, 16H), 2.0–1.5 (m, 4H), 1.4 (s, 6H), 1.3–0.9 (m, 6H), 0.8 (s, 9H) ppm.

EXAMPLE 11

The diols in Table VIII can be prepared by reaction of the appropriate olefin of the formula XV with 3-chloroperbenzoic acid using the procedure of Example 9.

TABLE VIII

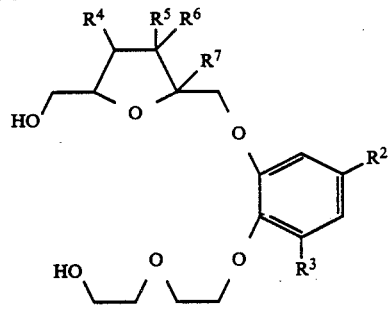

| R² | R³ | R⁴ | R⁵ | R⁶ | R⁷ |
|---|---|---|---|---|---|
| hydrogen | n-octyl | H | H | H | H |
| methyl | n-hexyl | CH₃ | CH₃ | H | H |
| t-octyl | hydrogen | CH₃ | H | H | H |
| ethyl | n-octyl | H | CH₃ | H | H |
| isobutyl | isopropyl | H | H | H | H |
| phenyl | ethyl | H | H | H | CH₃ |
| hydrogen | methyl | H | CH₃ | CH₃ | H |
| t-octyl | thiophenoxymethyl | H | H | H | H |
| n-decyl | hydrogen | H | H | H | H |

EXAMPLE 12

The diols in Table IX can be prepared by reaction of the appropriate product from Preparation 17 with the requisite epoxide of formula XII according to the procedure of Preparation 14, followed by treatment of the product with 3-chloroperbenzoic acid according to the procedure of Preparation 15.

TABLE IX

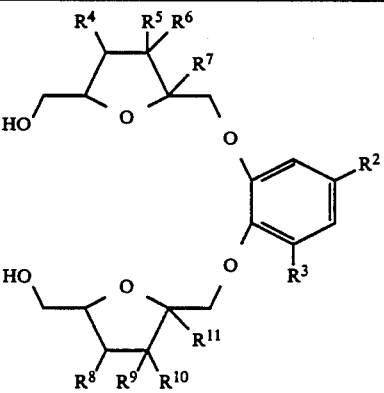

| R² | R³ | R⁴ | R⁵ | R⁶ | R⁷ | R⁸ | R⁹ | R¹⁰ | R¹¹ |
|---|---|---|---|---|---|---|---|---|---|
| methyl | n-octyl | H | CH₃ | H | H | CH₃ | H | H | H |
| t-octyl | ethyl | CH₃ | H | H | H | H | H | H | H |
| ethyl | isobutyl | H | H | H | H | CH₃ | H | H | H |
| t-octyl | methyl | H | H | H | H | CH₃ | CH₃ | H | H |

EXAMPLE 13

1-(2-[2-Hydroxyethoxy]ethoxy)-2-(5-hydroxymethyl-2-methyl-2-tetrahydrofuranylmethoxy)-4-t-octyl-6-thiophenoxymethylbenzene The product from Preparation 19 was reacted with 3.2 g (15 mmole) of 2-(2-[2-chloroethoxy]ethoxy)-tetrahydropyran and 2.13 g (15 mmole) of potassium carbonate in N,N-dimethylformamide, followed by hydrolysis with hydrochloric acid in methanol, using the procedure of Preparation 11, to give 0.54 g of the title compound as an oil. NMR(CDCl₃): 7.2 (m, 5H), 6.75 (s, 2H), 4.3–4.0 (m, 5H), 3.9–3.4 (m, 10H), 3.0 (s, 2H), 2.0 (m, 4H), 1.6 (s, 2H), 1.4 (d, 3H), 1.3 (s, 6H), 0.8 (s, 9H) ppm.

PREPARATION 1

1,2-Di(5-methoxycarbonyl-2-furylmethoxy)-4-t-octylbenzene

To a solution of 20.0 g (0.09 mole) of 4-t-octylcatechol and 33.0 g (0.19 mole) of methyl 5-chloromethyl-2-furoate (Annalen der Chemie, 580, 169 [1953]) in 473 ml of N,N-dimethylformamide was added 28 g (0.20 mole) of potassium carbonate. The resulting mixture was heated at 100° C. for 3 hours, and then it was poured onto a mixture of ice and 1N hydrochloric acid (1 liter). The mixture thus obtained was extracted with ethyl acetate, and the combined extracts were washed with water, followed by 5% potassium hydroxide, followed by water. The ethyl acetate solution was then evaporated in vacuo and the residual oil was triturated with hexane. The solid which formed was recovered by filtration to give 42 g (94% yield) of the title compound as a white solid. NMR(CDCl₃): 7.1 (d, 2H), 6.9 (q, 3H), 6.4 (d, 2H), 5.1 (d, 4H), 3.9 (s, 6H), 1.6 (s, 2H), 1.3 (s, 6H), 0.7 (s, 9H) ppm.

PREPARATION 2

The compounds in Table X were prepared by reaction of the appropriate catechol with methyl 5-chloromethyl-2-furoate or methyl 5-chloromethyl-4-methyl-2-furoate, using the procedure of Preparation 1.

TABLE X

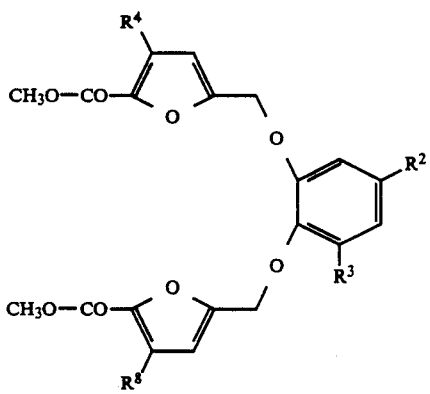

| R² | R³ | R⁴ | R⁸ | M.P. (°C.) | Yield (%) |
|---|---|---|---|---|---|
| hydrogen | hydrogen | H | H | 88–89 | 81 |
| t-butyl | hydrogen | H | H | 108–110 | 82 |
| n-octyl | hydrogen | H | H | — | 61 |
| t-octyl | methyl | H | H | oil | 90 |
| t-octyl | thiophenoxymethyl | H | H | oil | 62 |
| t-octyl | hydrogen | CH₃ | CH₃ | 62–63 | 48 |

PREPARATION 3

1,2-Di(5-methoxycarbonyl-2-tetrahydrofuranylmethoxy-4-t-octylbenzene

To a solution of 5.0 g (0.01 mole) of the product of Preparation 1 in a mixture of 300 ml of ethyl acetate and 100 ml of ethanol was added 0.5 g of 5% rhodium-on-alumina. The resulting mixture was stirred under an atmosphere of hydrogen at a pressure of ca. 12 kg/cm² for 4 hours and then it was filtered. The filtrate was evaporated in vacuo to give the title compound as an oil (4.8 g; 96% yield).

IR (neat): 1745 cm⁻¹.

NMR(CDCl₃): 6.9 (m, 3H), 4.6 (m, 4H), 4.2 (m, 4H), 3.8 (s, 6H), 2.2 (m, 8H), 1.8 (s, 2H), 1.5 (s, 6H), 0.8 (s, 9H) ppm.

PREPARATION 4

Hydrogenation of the appropriate product from Preparation 2 using the procedure of Preparation 3 afforded the products in Table XI, each of which was isolated as an oil.

TABLE XI

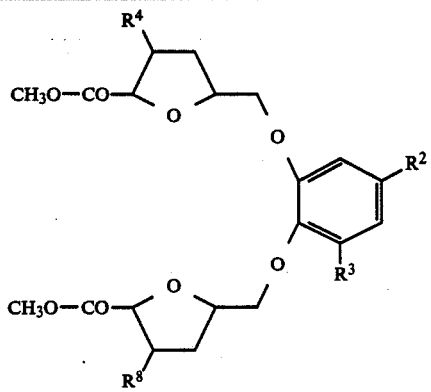

| R² | R³ | R⁴ | R⁸ | Yield (%) |
|---|---|---|---|---|
| hydrogen | hydrogen | H | H | 41 |
| t-butyl | hydrogen | H | H | 55 |
| n-octyl | hydrogen | H | H | 95 |
| t-octyl | methyl | H | H | 70 |
| t-octyl | hydrogen | CH₃ | CH₃ | 79 |

PREPARATION 5

COMPOUND III ($R$ is methyl; $R^1$ is t-butyl; $R^2$ is t-octyl; $R^3$, $R^4$, $R^5$, $R^6$, $R^7$, $R^8$, $R^9$, $R^{10}$ and $R^{11}$ are hydrogen)

A solution of the product of Example 4 (2.7 g, 60 mmole) and 2.26 g (60 mmole) of methyl 2,6-di(bromomethyl)-4-t-butylbenzoate in 50 ml of tetrahydrofuran was added dropwise during several hours to a refluxing suspension of 320 mg (130 mmole) of sodium hydride in 50 ml of tetrahydrofuran, under nitrogen. This mixture was heated for 6 hours under reflux, and then it was stirred at room temperature overnight. Aqueous (5%) tetrahydrofuran (10 ml) was then added dropwise. The solvent was removed by evaporation in vacuo and the residue was dissolved in chloroform. The chloroform solution was washed with water, followed by 1N hydrochloric acid, followed by saturated sodium chloride solution. The chloroform solution was dried (MgSO₄) and evaporated in vacuo to give an oil, which was purified by column chromatography over silica gel, eluting with 5% chloroform in ethyl acetate. This afforded 2.9 g of the title macrocycle as an oil (46% yield).

IR (neat): 1725 cm⁻¹.

NMR(CDCl₃): 7.4 (s, 2H), 6.9 (m, 3H), 4.7 (m, 4H), 4.5-3.3 (m, 15H), 1.9 (m, 10H), 1.4 (s, 15H), 0.8 (s, 9H) ppm.

PREPARATION 6

Reaction of methyl 2,6-di(bromomethyl)benzoate or methyl 2,6-di(bromomethyl)-4-t-butylbenzoate with the appropriate diol of the formula VI or VII, using the procedure of Preparation 5, afforded the compounds in Tables XII and XIII. In each case, the compound was isolated as an oil.

TABLE XII

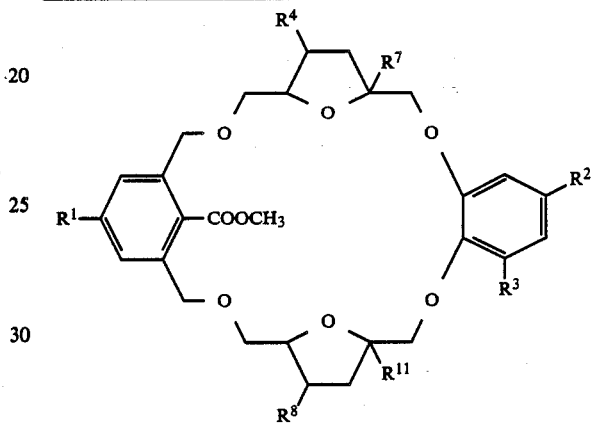

| R¹ | R² | R³ | R⁴ | R⁷ | R⁸ | R¹¹ | Yield (%) |
|---|---|---|---|---|---|---|---|
| H | H | H | H | H | H | H | 25 |
| H | t-butyl | H | H | H | H | H | 35 |
| H | t-octyl | H | H | H | H | H | 40 |
| t-butyl | t-butyl | H | H | H | H | H | 43 |
| t-butyl | n-octyl | H | H | H | H | H | 26 |
| t-butyl | t-octyl | methyl | H | H | H | H | 20 |
| t-butyl | t-octyl | H | CH₃ | H | CH₃ | H | 20 |
| H | t-octyl | H | CH₃ | H | CH₃ | H | 14 |
| t-butyl | t-butyl | H | H | CH₃ | H | CH₃ | 25 |
| H | t-butyl | H | H | CH₃ | H | CH₃ | 14 |
| t-butyl | t-octyl | H | H | CH₃ | H | CH₃ | 45 |
| H | t-octyl | H | H | CH₃ | H | CH₃ | 14 |
| t-butyl | phenyl | H | H | CH₃ | H | CH₃ | 25 |
| H | phenyl | H | H | CH₃ | H | CH₃ | 15 |
| t-butyl | t-octyl | methyl | H | CH₃ | H | CH₃ | 30 |

TABLE XIII

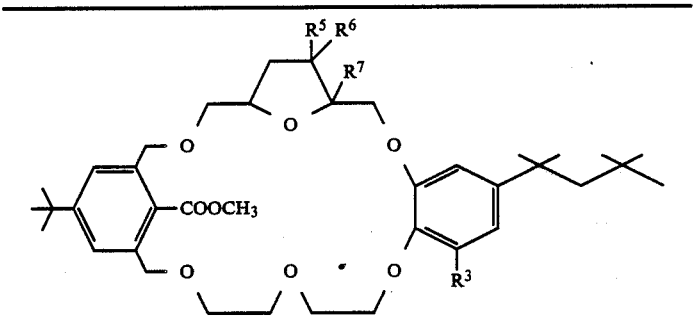

| R³ | R⁵ | R⁶ | R⁷ | Yield (%) |
|---|---|---|---|---|
| methyl | H | H | CH₃ | 40 |
| hydrogen | H | H | CH₃ | 56 |
| thiophenoxymethyl | H | H | CH₃ | 51 |
| methyl | CH₃ | CH₃ | H | 43 |

TABLE XIII-continued

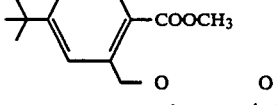

| R³ | R⁵ | R⁶ | R⁷ | Yield (%) |
|---|---|---|---|---|
| hydrogen | CH₃ | CH₃ | H | 40 |

PREPARATION 7

1,2-Di(2-Hydroxy-2-methyl-5-hexenyloxy)-4-t-butylbenzene

A mixture of 7.8 g (47 mmole) of 4-t-butylcatechol, 21.05 g (188 mmole) of 1,2-epoxy-2-methyl-5-hexene (prepared according to *Journal of the American Chemical Society* 87, 1361 [1965]) and 0.39 g (4.7 mmole) of piperidine was heated at 110° C. with stirring under nitrogen for 3 days. Additional piperidine (0.1 ml) was added and the mixture was heated at 125° C. for 5 days. The reaction mixture was cooled and dissolved in 200 ml of diethyl ether. The solution thus obtained was washed with water, followed by 5% potassium hydroxide solution, followed by water, and then it was dried (MgSO₄) and evaporated in vacuo. The residue was purified by column chromatography on silica gel, using chloroform as eluant to give 14.2 g (78% yield) of the title compound as a colorless oil.

NMR (CDCl₃): 6.9 (m, 3H), 5.9 (m, 2H), 5.0 (m, 4H), 4.9 (d, 4H), 3.1 (s, 2H), 2.4–1.5 (m, 8H), 1.4 (s, 15H) ppm.

PREPARATION 8

2-(2-Hydroxy-2-methyl-5-hexenyloxy)-6-methyl-4-t-octylphenol

A mixture of 10.5 g (44 mmole) of 3-methyl-5-t-octylcatechol, 11 g (90 mmole) of 1,2-epoxy-2-methyl-5-hexene and 0.75 ml of piperidine was heated at 120° C., with stirring, under nitrogen, for 7 days. The reaction mixture was cooled and dissolved in ether (300 ml), and the resulting solution was washed with water, followed by 1N hydrochloric acid, followed by saturated sodium chloride solution. The washed ethereal solution was dried (MgSO₄) and evaporated in vacuo, and the residue was purified by column chromatography on silica gel, eluting with chloroform. This afforded a 25% yield of the title compound as an oil.

NMR (CDCl₃): 6.8 (s, 2H), 6.2–5.5 (m, 1H), 5.2–4.8 (m, 2H), 3.9 (s, 2H), 2.3 (s, 3H), 2.2–1.7 (m, 6H), 1.4 (s, 6H) and 0.8 (s, 9H) ppm.

PREPARATION 9

By reaction of the appropriate catechol (IX) with the requisite epoxide (VII), and using the procedure of Preparation 8, the following compounds were prepared:

2-(2-hydroxy-2-methyl-5-hexenyloxy)-4-t-octylphenol (28% yield) and 2-(2-hydroxy-3,3-dimethyl-5-hexenyloxy)-6-methyl-4-t-octylphenol (85% yield).

PREPARATION 10

The compounds in Table XIV can be prepared by reaction of the appropriate catechol (IX) with the requisite epoxide (XII) using the procedure of Preparation 8.

TABLE XIV

(XIV)

| R² | R³ | R⁴ | R⁵ | R⁶ | R⁷ |
|---|---|---|---|---|---|
| hydrogen | n-octyl | H | H | H | H |
| methyl | n-hexyl | CH₃ | CH₃ | H | H |
| t-octyl | hydrogen | CH₃ | H | H | H |
| ethyl | n-octyl | H | CH₃ | H | H |
| isobutyl | isopropyl | H | H | H | H |
| phenyl | ethyl | H | H | H | CH₃ |
| hydrogen | methyl | H | CH₃ | CH₃ | H |
| t-octyl | thiophenoxymethyl | H | H | H | H |
| n-decyl | hydrogen | H | H | H | H |

PREPARATION 11

1-(2-[2-Hydroxyethoxy]ethoxy)-2-(2-hydroxy-2-methyl-5-hexenyloxy)-6-methyl-4-t-octylbenzene A mixture of the product of Preparation 8 (3.6 g, 11 mmole), 2.3 g (12 mmole) of 2-(2-[2-chloroethoxy]ethoxy)tetrahydropyran, 0.42 g (12 mmole) of potassium carbonate and 200 ml of N,N-dimethylformamide was heated at 140° C. with stirring for 18 hours. The reaction mixture was cooled, diluted with water and extracted with ethyl acetate. The extracts were washed successively with water and 1N hydrochloric acid and then they were evaporated in vacuo. The residue was dissolved in 300 ml of methanol containing 1 ml of 1N hydrochloric acid, and the resulting solution was stored at room temperature for 18 hours. The methanol was removed by evaporation in vacuo and the residue was dissolved in dichloromethane. The resulting solution was washed with water, dried (MgSO$_4$), and evaporated in vacuo. The residue was purified by column chromatography over silica gel, eluting with chloroform, to give 2.9 g of the title compound as an oil (60% yield).

NMR (CDCl$_3$): 6.8 (s, 2H), 6.2–5.5 (m, 1H), 5.2–4.8 (m, 2H), 4.2–3.5 (m, 12H), 2.2 (s, 3H), 2.2–1.6 (m, 6H), 1.4 (m, 9H) and 0.8 (s, 9H) ppm.

PREPARATION 12

Reaction of the appropriate phenol (XIV) with 2-(2-[2-chloroethoxy]ethoxy)tetrahydropyran, followed by acid-catalyzed hydrolysis using the procedure of Preparation 11, gave the following compounds:
1-(2-[2-hydroxyethoxy]ethoxy)-2-(2-hydroxy-2-methyl-5-hexenyloxy)-4-t-octylbenzene (63% yield),
1-(2-[2-hydroxyethoxy]ethoxy)-2-(2-hydroxy-3,3-dimethyl-5-hexenyloxy)-6-methyl-4-t-octylbenzene (50% yield) and
1-(2-[2-hydroxyethoxy]ethoxy)-2-(2-hydroxy-3,3-dimethyl-5-hexenyloxy)-4-t-octylbenzene (60% yield).

PREPARATION 13

The compounds in Table XV can be prepared by reaction of the appropriate product from Preparation 10 with 2-(2-[2-chloroethoxy]ethoxy)tetrahydropyran, followed by acid-catalyzed hydrolysis, using the procedure of Preparation 11.

TABLE XV

| R$^2$ | R$^3$ | R$^4$ | R$^5$ | R$^6$ | R$^7$ |
|---|---|---|---|---|---|
| hydrogen | n-octyl | H | H | H | H |
| methyl | n-hexyl | CH$_3$ | CH$_3$ | H | H |
| t-octyl | hydrogen | CH$_3$ | H | H | H |
| ethyl | n-octyl | H | CH$_3$ | H | H |
| isobutyl | isopropyl | H | H | H | H |
| phenyl | ethyl | H | H | H | CH$_3$ |
| hydrogen | methyl | H | CH$_3$ | CH$_3$ | H |
| t-octyl | thiophenoxymethyl | H | H | H | H |
| n-decyl | hydrogen | H | H | H | H |

PREPARATION 14

1-Benzyloxy-2-(2-hydroxy-2-methyl-5-hexenyloxy)-4-t-octylbenzene

A mixture of 7.4 g (23.7 mmole) of 2-benzyloxy-5-t-octylphenol, 5.3 g (47.4 mmole) of 1,2-epoxy-2-methyl-5-hexene and 3.27 g (23.7 mmole) of potassium carbonate was heated at 120° C., with stirring, under nitrogen, for 48 hours. The cooled reaction mixture was extracted with ethyl acetate, and the resulting solution was washed with water followed by saturated sodium chloride solution. Evaporation of the washed ethyl acetate solution in vacuo, followed by purification of the residue by column chromatography on silica gel, eluting with 9:1 toluene-ethyl acetate, gave 8.33 g of the title compound as an oil.

NMR (CDCl$_3$): 7.35 (m, 5H), 6.9 (m, 3H), 5.8 (m, 1H), 5.0 (m, 4H), 3.8 (s, 2H), 2.5–1.6 (m, 7H), 1.3 (s, 6H), 1.25 (s, 3H), 0.8 (s, 9H) ppm.

PREPARATION 15

1-Benzyloxy-2-(5-hydroxymethyl-2-methyl-2-tetrahydrofuranylmethoxy)-4-t-octylbenzene The title compound was prepared in 46% yield by treatment of the product of Preparation 14 with 2 molar equivalents of 3-chloroperbenzoic acid in dichloromethane solution at room temperature for 72 hours.

NMR (CDCl$_3$): 7.3 (m, 5H), 6.8 (m, 3H), 5.0 (d, 2H), 4.6 (s, 1H), 4.1 (m, 1H), 3.8 (s, 2H), 3.5 (m, 2H), 2.2–1.6 (m, 6H), 1.4 (s, 9H), 0.8 (s, 9H) ppm.

PREPARATION 16

2-(5-Hydroxymethyl-2-methyl-2-tetrahydrofuranylmethoxy)-4-t-octylphenol

A mixture of 4 g (9.1 mmole) of 1-benzyloxy-2-(5-hydroxymethyl-2-methyl-2-tetrahydrofuranylmethoxy)-4-t-octylbenzene, 1 g of 10% palladium-on-carbon and 75 ml of ethanol was shaken under an atmosphere of hydrogen at ca. 4 kg/cm$^2$ for 3 hours. The resulting mixture was filtered, and the filtrate was evaporated in vacuo to give 3.7 g of the title compound as an oil.

NMR (CDCl$_3$): 6.9 (s, 3H), 4.3–3.5 (m, 7H), 1.9 (m, 4H), 1.6 (s, 2H), 1.3 (s, 9H), 0.7 (s, 9H) ppm.

PREPARATION 17

The compounds in Table XVI can be prepared by reaction of the appropriate benzyl ether of the formula XVII with the requisite epoxide of the formula XII, followed by treatment with 3-chloroperbenzoic acid, followed by hydrogenolysis, according to the procedures of Preparations 14, 15 and 16 respectively.

TABLE XVI

| R$^2$ | R$^3$ | R$^4$ | R$^5$ | R$^6$ | R$^7$ |
|---|---|---|---|---|---|
| methyl | n-octyl | H | CH$_3$ | H | H |
| t-octyl | ethyl | CH$_3$ | H | H | H |
| ethyl | isobutyl | H | H | H | H |
| t-octyl | methyl | H | H | H | H |

PREPARATION 18

2-(5-Hydroxymethyl-2-methyl-2-tetrahydrofuranylmethoxy)-6-morpholinomethyl-4-t-octylphenol A solution of 3.7 g (10 mmole) of 2-(5-hydroxymethyl-2-methyl-2-tetrahydrofuranylmethoxy)-4-t-octylphenol, 1 ml (12 mmole) of morpholine and 0.35 g (12 mmole) of paraformaldehyde in 25 ml of isopropanol was heated under reflux for 18 hours. The solvent was removed by evaporation in vacuo and the residue was extracted with diethyl ether. The resulting ethereal solution was washed with water, followed by saturated sodium chloride solution, and then dried (MgSO$_4$) and evaporated in vacuo. The residue was purified by chromatography over silica gel, eluting with ethyl acetate, to give 2.31 g of the title compound as an oil.

NMR (CDCl$_3$): 6.8 (d, 2H), 6.6 (d, 1H), 4.2 (s, 1H), 3.9–3.5 (m, 11H), 2.5 (m, 4H), 2.2–1.7 (m, 4H), 1.6 (s, 2H), 1.3 (m, 9H), 0.7 (s, 9H) ppm.

PREPARATION 19

2-(5-Hydroxymethyl-2-methyl-2-tetrahydrofuranylmethoxy)-6-thiophenoxymethyl-4-t-octylphenol A solution of 2.3 g (5 mmole) of 2-(5-hydroxymethyl-2-methyl-2-tetrahydrofuranylmethoxy)-6-morpholinomethyl-4-t-octylphenol and 0.85 g (7.7 mmole) of thiophenol in 25 ml of N,N-dimethylformamide was heated at 125° C. for 48 hours under nitrogen. The cooled reaction mixture was diluted with ethyl acetate and then it was washed with water, followed by 1N hydrochloric acid, followed by saturated sodium chloride solution. The resulting solution was dried (MgSO$_4$) and evaporated to give 3.4 g of an oil containing the title compound and thiophenol.

NMR (CDCl$_3$): 7.6–7.0 (m), 6.8 (s, 2H), 4.3–3.5 (m, 7H), 1.9 (m, 4H), 1.6 (s, 2H), 1.3 (d, 9H), 0.7 (s, 9H) ppm.

PREPARATION 20

2-(2-[2-Hydroxyethoxy]ethoxy)-5-t-octylbenzaldehyde

A mixture of methyl 5-t-octylsalicylate (75.5 g, 0.286 mole), 2-(2-[2-chloroethoxy]ethoxy)tetrahydropyran (71.56 g, 0.343 mole), potassium carbonate (39.5 g, 0.286 mole) and N,N-dimethylformamide (250 ml) was heated at 140° C., under nitrogen, for 18 hours, with stirring. The mixture was cooled, diluted with ether, and then washed liberally with saturated sodium chloride solution. The ethereal solution was dried (MgSO$_4$) and evaporated in vacuo to give an oil, which was chromatographed on silica gel to give 28.5 g of methyl 2-(2-[2-(2-tetrahydropyranyloxy)ethoxy]ethoxy)-5-t-octylsalicylate and 42 g of 2-(2-[2-tetrahydropyranyloxy]ethoxy)ethyl 2-(2-[2-(2-tetrahydropyranyloxy)ethoxy]ethoxy)-5-t-octylsalicylate.

The latter ester (42 g, 0.07 mole) was dissolved in a small amount of dry tetrahydrofuran, and the solution was added to a slurry of lithium aluminum hydride (4 g, 0.1 mole) in tetrahydrofuran. The mixture was heated under reflux for 18 hours and then cooled. To the cooled mixture was added aqueous tetrahydrofuran, dropwise, followed by saturated sodium sulfate, followed by solid sodium sulfate. The resulting mixture was filtered and the filtrate was evaporated in vacuo to give 35.7 g (99% yield) of 2-(2-[2-(2-tetrahydropyranyloxy)ethoxy]ethoxy)-5-t-octylbenzyl alcohol as an oil.

The above benzyl alcohol (37 g, 0.08 mol) in dichloromethane (150 ml) was added dropwise to a suspension of pyridinium dichromate (36.25 g, 0.14 mole, *Tetrahedron Letters*, 399 [1979]) in dichloromethane (250 ml), with stirring. Stirring was continued overnight, and then the reaction mixture was diluted with ether and filtered through a magnesium sulfate:silica gel pad. The filtrate was washed with 1N hydrochloric acid and then it was evaporated in vacuo to give 31.2 g (87% yield) of 2-(2-[2-(2-tetrahydropyranyloxy)ethoxy]ethoxy)-5-t-octylbenzaldehyde, as an oil.

The above benzaldehyde was dissolved in methanol (400 ml) containing 1N hydrochloric acid (50 ml) and the mixture was stirred at room temperature for 3 hours. The methanol was removed by evaporation in vacuo, and the residue was extracted with dichloromethane. The extracts were evaporated in vacuo, to give the title compound as an oil (23.6 g).

PREPARATION 21

2-(2-[2-Hydroxyethoxy]ethoxy)-5-t-octylphenoxy Formate

The product of Preparation 20 (23.6 g, 0.073 mole) in dichloromethane (300 ml) was added to a solution of 3-chloroperbenzoic acid (22.3 g, 0.11 mole) in dichloromethane (200 ml) during 1 hour. The reaction mixture was stored at room temperature for 18 hours and then it was heated under reflux for 5 hours. The reaction mixture was cooled to ca. 0° C. and filtered. The volume of the filtrate was reduced to ca. 50 ml and then ether was added. The resulting mixture was washed with sodium bicarbonate solution, sodium bisulfite solution and sodium chloride solution. The ethereal solution was then dried (MgSO$_4$) and evaporated in vacuo to give the title compound as an oil.

PREPARATION 22

2-(2-[2-Hydroxyethoxy]ethoxy)-5-t-octylphenol

The product of Preparation 21 was dissolved in methanol (400 ml) containing concentrated hydrochloric acid (4 ml) and the mixture was heated under reflux for 4 hours. The methanol was removed by evaporation in vacuo and the residue was dissolved in ethyl acetate. The ethyl acetate solution was dried (MgSO$_4$) and then it was concentrated to ca. 50 ml. Petroleum ether (400 ml) was added and the resulting mixture was cooled. The solid was recovered by filtration to give 12.0 g (60% yield) of the title compound as a white crystalline solid, m.p. 112°–113° C.

NMR (CDCl$_3$): 6.9 (m, 3H), 4.1 (m, 2H), 3.9–3.5 (m, 7H), 1.6 (s, 2H), 1.3 (s, 6H) and 0.8 (s, 9H) ppm.

PREPARATION 23

2-Bromo-5-t-butyl-1,3-dimethylbenzene

To a solution of 200 g (1.23 mole) 5-t-butyl-1,3-dimethylbenzene and 83 ml (1.23 mole) propylene oxide in 500 ml of methylene chloride at 15° C. or less, 63 ml (1.23 mole) bromine was added dropwise while maintaining the solution temperature at 15° C. or less. The reaction mixture was allowed to warm to 25° C. overnight. A 200 ml solution of 5% by weight of potassium hydroxide in water was added and the resulting two phase system was stirred for 1 hr at 25° C. The organic phase was washed with water and dried over anhydrous magnesium sulfate. After solvent evaporation an oil was left which when crystallized from methanol gave 265 g (87% yield) of the title compound after drying in vacuo. The oil could also be purified by distilling at 61°–70° C. under a reduced pressure of 0.25 mm of mercury.

NMR (CDCl$_3$): 1.3 (s, 9H), 2.4 (s, 6H) and 7.0 (s, 2H).

PREPARATION 24

4-t-Butyl-2,6-dimethylbenzoic Acid

To 72.9 g (3 moles) magnesium in 473 ml of diethyl ether was added a small portion taken from a solution of 482 g (2 moles) 4-t-butyl-2,6-dimethylbromobenzene in 86 ml (1 mole) 1,2-dibromoethane with stirring. When the Grignard reaction commenced, the remaining solution was added at a rate to maintain reflux with external cooling. Following addition, the reaction mixture was maintained at reflux overnight, cooled and poured over solid carbon dioxide. The reaction mixture was acidified to pH 1.5 with concentrated hydrochloric acid to give the title acid which was extracted into 500 ml of diethyl ether. Replacement of the ether by hexane gave the title compound as a white solid (261 g, 63% yield, m.p. 160°–164° C.). See Journal of Organic Chemistry, 23, 1161 (1950).

NMR (CDCl$_3$): 1.35 (s, 9H), 2.4 (s, 6H) and 7.01 (s, 2H) ppm.

PREPARATION 25

Methyl 4-t-Butyl-2,6-dimethylbenzoate

To 50 g (0.26 moles) of 4-t-butyl-2,6-dimethylbenzoic acid in 250 ml methylene chloride was added 25 ml (0.34 mole) of thionyl chloride at 25° C. After stirring overnight at 25° C. the solvent and remaining thionyl chloride were evaporated in vacuo. The resulting white solid was dissolved in 50 ml tetrahydrofuran and added dropwise to 250 ml of methanol containing 2 ml of pyridine. After heating the reaction mixture to reflux for 30 minutes the solvents were evaporated in vacuo and the residue was dissolved in 200 ml ethyl acetate and 100 ml of water was added. The organic phase was separated and washed with 100 ml saturated aqueous sodium bicarbonate, 50 ml water and 25 ml brine; then dried over anhydrous magnesium sulfate and evaporated to an oil. The oil was distilled in vacuo at 104°–8° C. at 1.2 mm of mercury to obtain 43 g (81% yield) of the title compound.

NMR (CDCl$_3$): 1.3 (s, 9H), 2.4 (s, 6H), 3.9 (s, 3H) and 7.0 (s, 2H).

PREPARATION 26

Methyl 2,6-di(Bromomethyl)-4-t-butylbenzoate

Methyl 4-t-butyl-2,6-dimethylbenzoate (22 g, 0.1 mole), 1,3-dibromo-5,5-dimethylhydantoin (31.5 g, 0.11 moles) and benzoyl peroxide (50 mg) in carbon tetrachloride (300 ml) were heated to reflux and irradiated with a 275 watt sunlamp. After 1.5 hours of irradiation at reflux the yellow color of the reaction mixture had been dispersed. The reaction mixture was cooled to 25° C. and the hydantoin was removed by filtering. The carbon tetrachloride was evaporated in vacuo. The desired material crystallized from petroleum ether to give 18.4 g, 49% yield, m.p. 99°–100° C., of the title compound.

NMR (CDCl$_3$): 1.35 (s, 9H), 4.0 (s, 3H), 4.6 (s, 4H) and 7.35 (s, 2H) ppm.

Methyl 2,6-di(bromomethyl)benzoate was prepared in analogous fashion, m.p. 76°–79° C.

NMR (CDCl$_3$): 7.4 (s, 3H), 4.6 (s, 4H) and 4.0 (s, 3H) ppm.

PREPARATION 27

3-Methyl-5-(t-octyl)catechol

A mixture of 3-methylcatechol (56 g, 0.45 mole) and 10 drops of concentrated sulfuric acid was heated to 100° C. Di-isobutylene (2,4,4-trimethyl-2-pentene) (67 g, 0.6 mole) was added dropwise over a 15 min. period. After stirring at 100° C. for an additional 20 min., the temperature was raised to 130° C. and maintained at that temperature for 2 hours. The reaction mixture was allowed to cool to 50° C. and ethyl acetate (0.5 liter) was added. The resulting organic solution was washed 3 times with 500 ml of saturated aqueous sodium carbonate, once with 1N hydrochloric acid (0.2 liter), water (0.2 liter) and brine (0.1 liter). The organic solution was dried over anhydrous magnesium sulfate and treated with activated carbon. The solution was filtered and evaporated to an orange oil. Addition of 150 ml petroleum ether gave a white solid of the title compound (76 g, 72% yield).

NMR (CDCl$_3$): 6.7 (s, 2H), 2.2 (s, 3H), 1.7 (s, 2H), 1.3 (s, 6H) and 0.8 (s, 9H) ppm. IR (CH$_2$Cl$_2$): 3530, 2950 and 1475 cm$^{-1}$.

PREPARATION 28

3-Methyl-5-(3,3-dimethylbutanoyl)catechol

While 3-methylcatechol (11.5 g, 0.093 mole) was melted at 85° C., 3,3-dimethylbutanoyl chloride (25 g, 0.186 mole) was added dropwise over 15 min. The resulting mixture was heated to 110° C. for 1.5 hrs. to complete the reaction. The mixture was cooled to 30° C., then dissolved in 25 ml carbon disulfide at 30° C. containing 3-methylcatechol (11.5 g, 0.09 mole). The resulting solution was added dropwise to a stirred suspension of aluminum trichloride (62 g, 0.465 mole) in carbon disulfide (110 ml) at 40° C. Following addition, the reaction mixture was stirred for 1 hr. at 25° C., then heated to 80° C. and the carbon disulfide removed by distillation. After solvent removal, the residual material was heated to 140°–145° C. for 3.5 hrs. then cooled in an ice bath and quenched with 200 ml of a 1:1 mixture of concentrated hydrochloric acid and water. Diethyl ether (150 ml) was added and the layers were separated. The aqueous layer was extracted further with 150 ml of diethyl ether. The combined organic portions were washed with two 50 ml portions of water, two 50 ml portions of 5% weight to volume sodium bicarbonate, 50 ml water and 25 ml brine. The diethyl ether was evaporated to give a brown oil which crystallized from 100 ml petroleum ether to yield the product as a light yellow solid (16.5 g, 40% yield, m.p. 139°-143° C.).

NMR (CDCl₃): 7.3 (q, 2H), 2.7 (s, 2H), 2.3 (s, 3H) and 1.05 (s, 9H) ppm. IR (KBr disc): 3448, 3180, 2940, 1653 and 1595 cm⁻¹.

PREPARATION 29

3-Morpholinomethyl-5-t-octylcatechol

To paraformaldehyde (40 g, 1.3 mole) in 100 ml isopropanol at 25° C. was added morpholine (88 ml) in 0.5 liter isopropanol. The reaction mixture was refluxed for 30 minutes to effect solution. To the solution 4-t-octylcatechol (222 g, 1.0 mole) dissolved in 0.5 liter isopropanol was added dropwise while maintaining the solution temperature at 60° C. The reaction mixture was stirred at reflux overnight. The reaction was cooled to 25° C. and the solvent was removed in vacuo to give a white solid which was triturated with 750 ml petroleum ether and collected. Overall yield from two crops was 86%, 280 g.

NMR (CDCl₃): 8.0 (s, 2H), 6.9 (d, 1H), 6.5 (d, 1H), 3.7 (m, 6H), 2.5 (m, 4H) 1.6 (s, 2H), 1.3 (s, 6H) and 0.8 (s, 9H) ppm.

PREPARATION 30

3-Thiophenoxymethyl-5-t-octylcatechol

A suspension of 3-morpholinomethyl-5-t-octylcatechol (564 g, 1.76 mole) and 193.4 g (1.76 mole) benzenethiol in 0.8 liter dimethylformamide was kept at 130° C. under a nitrogen atmosphere for 20 hours. The reaction mixture was cooled to 25° C. and diluted with 3000 ml diethyl ether. The resulting solution was washed in turn with 3×1000 ml water, 500 ml 10% hydrochloric acid, 500 ml water and 500 ml brine. The washed solution was dried over anhydrous magnesium sulfate and evaporated in vacuo to a yellow oil (548.9 g, 91% yield) of the title compound.

NMR (CDCl₃): 7.2 (m, 5H), 6.8 (d, 1H), 6.5 (d, 1H), 5.8 (bs, 2H), 4.1 (s, 2H), 1.6 (s, 2H), 1.2 (s, 6H) and 0.6 (s, 9H) ppm.

I claim:

1. A macrocyclic polyether compound selected from the group consisting of

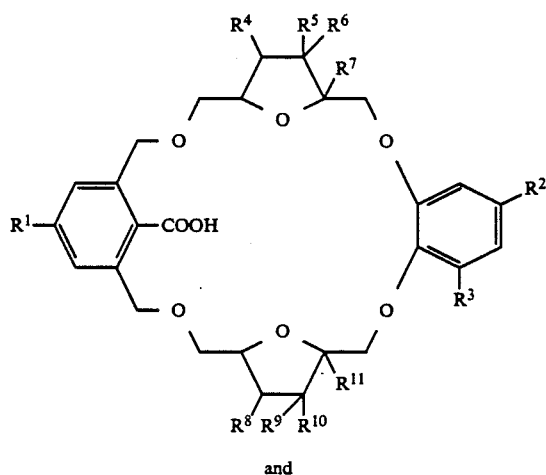

and

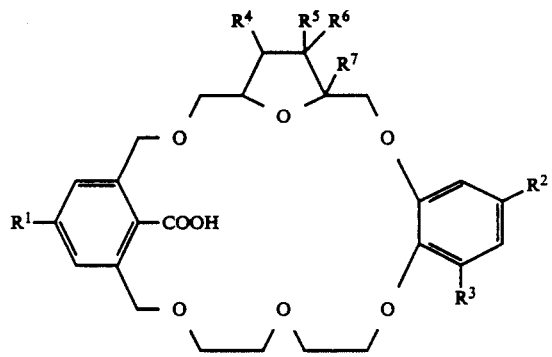

-continued and the pharmaceutically-acceptable base salts thereof, wherein $R^1$ is selected from the group consisting of hydrogen and t-butyl;

$R^2$ is selected from the group consisting of hydrogen, alkyl having 1 to 10 carbons and phenyl;

$R^3$ is selected from the group consisting of hydrogen, alkyl having 1 to 8 carbons and thiophenoxymethyl;

and $R^4$, $R^5$, $R^6$, $R^7$, $R^8$, $R^9$, $R^{10}$ and $R^{11}$ are each selected from the group consisting of hydrogen and methyl, provided that not more than two of $R^4$, $R^5$, $R^6$ and $R^7$ are methyl and not more than two of $R^8$, $R^9$, $R^{10}$ and $R^{11}$ are methyl.

2. A compound according to claim 1 of the formula

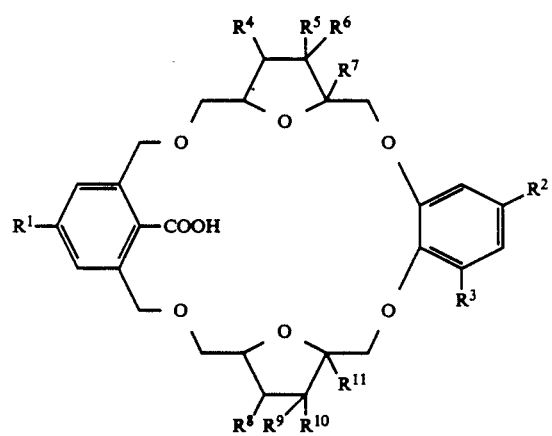

and the pharmaceutically-acceptable base salts thereof.

3. A compound according to claim 2, wherein $R^4$ and $R^8$ are the same, $R^5$ and $R^9$ are the same, $R^6$ and $R^{10}$ are the same and $R^7$ and $R^{11}$ are the same.

4. A compound according to claim 3, wherein $R^3$ is hydrogen or said alkyl.

5. A compound according to claim 4 wherein $R^1$ is t-butyl.

6. A compound according to claim 5, wherein $R^4$, $R^5$, $R^6$, $R^7$, $R^8$, $R^9$, $R^{10}$ and $R^{11}$ are each hydrogen.

7. A compound according to claim 6, wherein $R^3$ is hydrogen.

8. A compound according to claim 7, wherein $R^2$ is t-octyl.

9. A compound according to claim 5, wherein $R^4$, $R^5$, $R^6$, $R^8$, $R^9$ and $R^{10}$ are each hydrogen and $R^7$ and $R^{11}$ are each methyl.

10. A compound according to claim 9, wherein $R^3$ is hydrogen.

11. A compound according to claim 10, wherein $R^2$ is t-octyl.

12. A compound according to claim 3, wherein $R^3$ is thiophenoxymethyl.

13. A compound according to claim 12, wherein $R^4$, $R^5$, $R^6$, $R^7$, $R^8$, $R^9$, $R^{10}$ and $R^{11}$ are each hydrogen.

14. A compound according to claim 1 of the formula

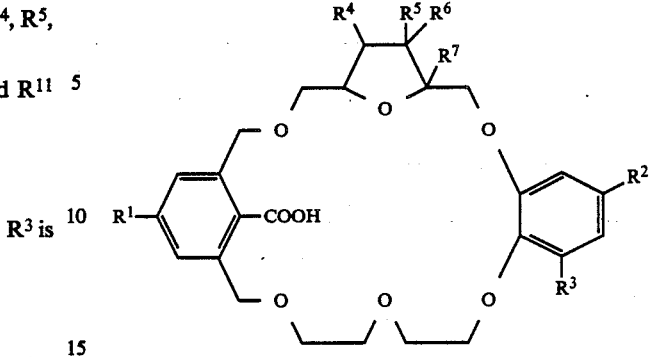

and the pharmaceutically-acceptable base salts thereof.

15. A compound according to claim 14, wherein $R^3$ is hydrogen or said alkyl.

16. A compound according to claim 15, wherein $R^1$ is t-butyl.

17. A compound according to claim 16, wherein $R^4$, $R^5$ and $R^6$ are hydrogen and $R^7$ is methyl.

18. A compound according to claim 17, wherein $R^2$ is t-octyl and $R^3$ is hydrogen or methyl.

19. A method of increasing the efficiency of feed utilization in ruminant animals which comprises administering orally to said animals an effective propionate-increasing amount of a macrocyclic polyether compound according to claim 1.

20. The method according to claim 19, wherein said ruminant animals are cattle.

* * * * *